United States Patent [19]
Yamada et al.

[11] Patent Number: 5,885,824
[45] Date of Patent: Mar. 23, 1999

[54] RECOMBINANT GENOMIC CLONE ENCODING THE HISTAMINE H2 RECEPTOR, METHODS FOR PRODUCTION THEREOF, AND PROTEIN PRODUCED THEREFROM

[75] Inventors: Tadataka Yamada; Ira Gantz, both of Ann Arbor, Mich.

[73] Assignee: The Regents of the University of Michigan, Ann Arbor, Mich.

[21] Appl. No.: 103,170

[22] Filed: Sep. 9, 1993

Related U.S. Application Data

[63] Continuation of Ser. No. 633,060, Dec. 24, 1990, abandoned.

[51] Int. Cl.⁶ .............................. C12N 1/20; C12N 15/00; C07H 17/00; C07K 14/00
[52] U.S. Cl. .................................... 435/252.3; 435/320.1; 536/23.5; 530/350
[58] Field of Search ..................... 530/300, 350; 536/23.1, 23.5; 435/69.1, 69.4, 320.1, 252.3; 935/78

[56] References Cited

PUBLICATIONS

Peralta et al 1987 B Embo J 6(13):3923.
Kobilka et al. 1987 A J. Biol. Chem 262(32):15796.
Hershey & Krause 1990, Science 247:958.
Kobilka et al. 1987B Science 238:650.
Yokota et al 1989 J. Biol. Chem. 264(30):17649.
Frielle et al 1987 PNAS 84:7920–7924.
Traiffort et al 1992 PNAS 89:2649.
Yamashita et al. 1991 PNAS 88: 11515.
Wolfe et al. 1988, New England J. Med. 319:1707–1715.

*Primary Examiner*—Karen Cochrane Carlson
*Attorney, Agent, or Firm*—Oblon, Spivak, McClelland, Maier & Neustadt, P.C.

[57] ABSTRACT

Recombinant genomic clones encoding histamine H1, H2 and H3 receptors, recombinant H1, H2 and H3 receptors, and methods for obtaining these.

8 Claims, 8 Drawing Sheets

```
  1  ATGGCACCCAATGGCACAGCCTCTTCCTTTTGCCTGGACTCTACCGCATGCAAGATCACC   60
       AT T T  C                      T         C TC   G     T

61  ATCACCGTGGTCCTTGCGGTCCTCATCCTCATCACCGTTGCTGGCAATGTGGTCGTCTGT  120
       G  G      CA T              A C C           G     C

121  CTGGCCGTGGGCTTGAACCGCCGGCTCCGCAACCTGACCAATTGTTTCATCGTGTCCTTG  180
         T   C                   GT  T C C    T   G T

181  GCTATCACTGACCTGCTCCTCGGCCTCCTGGTGCTGCCCTTCTCTGCCATCTACCAGCTG  240
        T  C T                       G T              A

241  TCCTGCAAGTGGAGCTTTGGCAAGGTCTTCTGCAATATCTACACCAGCCTGGATGTGATG  300
              G       C    A              T   T

301  CTCTGCACAGCCTCCATTCTTAACCTCTTCATGATCAGCCTCGACCGGTACTGCGCTGTC  360
        G   G    C C                           T

361  ATGGACCCACTGCGGTACCCTGTGCTGGTCACCCCAGTTCGGGTCGCCATCTCTCTGGTC  420
       CT  C     C         TA      C       G     T

421  TTAATTTGGGTCATCTCCATTACCCTGTCCTTTCTGTCTATCCACCTGGGGTGGAACAGC  480
              C                C         T T

481  AGGAACGAGACCAGCAAGGGCAATCATACCACCTCTAAGTGCAAAGTCCAGGTCAATGAA  540
        T       GTTT    C   TTC C                      CTTG

541  GTGTACGGGCTGGTGGATGGGCTGGTCACCTTCTACCTCCCGCTACTGATCATGTGCATC  600
        T CT                    G     G  G

601  ACCTACTACCGCATCTTCAAGGTCGCCCGGGATCAGGCCAAGAGGATCAATCACATTAGC  660
                    A T         C            C    GG

661  TCCTGGAAGGCAGCCACCATCAGGGAGCACAAAGCCACAGTGACACTGGCCGCCGTCATG  720
             T   TG                              T A  G

721  GGGGCCTTCATCATCTGCTGGTTTCCCTACTTCACCGCGTTTGTGTACCGTGGGCTGAGA  780
         A    A  C                TT  T          A
```

*FIG. 1A(1)*

781 GGGGATGATGCCATCAATGAG GTGTTAGAAGCCATCGTTCTGTGGCTGGGCTATGCCAAC 840
                           CT  T         G

841 TCAGCCCTGAACCCCATCCTGTATGCTGCGCTGAACAGAGACTTCCGCACCGGGTACCAA 900
      G        T          CA A                  G CA       G

901 CAGCTCTTCTGCTGCAGGCTGGCCAACCGCAACTCCCACAAAACTTCTCTGAGGTCCAAC 960
           C       C    G A   TG   GG                    G

961 GCCTCTCAGCTGTCCAGGACCCAAAGCCGAGAACCCAGGCAACAGGAAGAGAAACCCCTG 1020
    AG      G    AT              T           GG            G

1021 AAGCTCCAGGTGTGGAGTGGGACAGAAGTCACGGCCCCCCAGGGAGCCACAGACAGGTAA 1080
                    G     A    T GA

*FIG. 1A(2)*

1   MAPNGTASSFCLDSTACKITITVVLAVLILITVAGNVVVCLAVGLNRRLRNLTNCFIVSL   60
     IS         PP R  VS  T   I           S      F

61  AITDLLLGLLVLPFSAIYQLSCKWSFGKVFCNIYTSLDVMLCTASILNLFMISLDRYCAV  120
    S             F      R

121 MDPLRYPVLVTPVRVAISLVLIWVISITLSFLSIHLGWNSRNETSKGNHTTSKCKVQVNE  180
       T    I      V                          SF    IP       L

181 VYGLVDGLVTFYLPLLIMCITYYRIFKVARDQAKRINHISSWKAATIREHKATVTLAAVM  240
             V             I        H MG       G

241 GAFIICWFPYFTAFVYRGLRGDDAINEVLEAIVLWLGYANSALNPILYAALNRDFRTGYQ  300
              V      K       AF V              T    A

301 QLFCCRLANRNSHKTSLRSNASQLSRTQSREPRQQEEKPLKLQVWSGTEVTAPQGATDR*  360
       R   P SH AQE     S    A N     MR                     R

*FIG. 1B*

```
-187                                                    CTAGAAAACAGTCGTCGGGCAGTTATTGTAACCTCCCCAGTCTGGACATTTTCTTTTGGCTCCATTAGGAGCCTA
-100  GAGCCCAGCGGTTGACATCATTGACACACTGGGGAGCTGGATGAGAAGTCAGGGGCTGTGGGCAGAGCCGTGGCAGAGGCCGTAGGATCCCAGG

1       ATGATATCTAACGGCACAGGTCTCTTCCTTTGTCTGGACTCTCCCATGCGAGGATCACTGTCAGGTGTCCTCACTGTCCTCATCCTC
   1       M  I  S  N  G  T  G  S  S  F  C  L  D  S  P  P  C  R  I  T  V  S  V  V  L  T  V  L  I  L

100       ATCACCATCGCCGGCAATGTGGTCTGCCTGGCTGTGGGCCTGAACCGCCGGCTCCGCAGTCTGACTAACTGCTTCATTGTCGTTG
  31       I  T  I  A  G  N  V  V  C  L  A  V  G  L  N  R  R  L  R  S  L  T  N  C  F  I  V  S  L

200       GCTATCACGGATCTGCTCCTCGGCCTCCTGGTGCTGCCTTTCTCGGCCTTCTACCAGCTATCCTGCAGGTGGAGCTTCGGCAAAGTCTTC
  62       A  I  T  D  L  L  L  G  L  L  V  L  P  F  S  A  F  Y  Q  L  S  C  R  W  S  F  G  K  V  F

300       TGCAATATCTATACCAGCTTGGATGTGATGCTGTGCACGGCCTCCATCCTCAACCTCTTCATGATCAGCTTGACCGGTACTGCGCTGTC
  93       C  N  I  Y  T  S  L  D  V  M  L  C  T  A  S  I  L  N  L  F  M  I  S  L  D  R  Y  C  A  V

400       ACTGACCCCCTGCCTATCACCCCAGTCCGGCGTGCCGTCTCTCTTGTCTTAATTGGGTCATCTCCATCACCCTGTCC
 124       T  D  P  L  R  Y  P  V  L  I  T  P  V  R  V  A  V  S  L  V  L  I  W  V  I  S  I  T  L  S

500       TTCCTGTCTATTCATCTGGGGTGGAACAGCAGGAATGAGACCAGTTCAATCACACCATTCCCAAGTGCAAAGTCCAGGTCAACTTG
 155       F  L  S  I  H  L  G  W  N  S  R  N  E  T  S  S  F  N  H  T  I  P  K  C  K  V  Q  V  N  L

600       GTGTATGGCTTGGTGGATGGGCTGGTCACCTTCTACCTTCTACCTGCTGCTGGTCATGTGCATCACCTACTACCGCATCTTCAAGATTGCCCGG
 186       V  Y  G  L  V  D  G  L  V  T  F  Y  L  P  L  L  V  M  C  I  T  Y  Y  R  I  F  K  I  A  R
```

*FIG. 2A*

```
 700       AGGATCCATGACCAGGCCAAGCACATGGGCTCCTGGAAGGCAGCTACCATTGGGGAGCACAAAGCCACAGTGACACTGGCTGCAGTGATG
 217       D   Q   A   K   R   I   H   H   M   G   S   W   K   A   A   T   I   G   E   H   K   A   T   V   T   L   A   A   V   M

800       GGAGCCTTCATCATATGCTGGTTCCCCTACTTTACTGTGTTTGTTTACCGTGGGCTGAAAGGGGATGATGCCATCAATGAGGCTTTTGAA
 248       G   A   F   I   I   C   W   F   P   Y   F   T   V   F   V   Y   R   G   L   K   G   D   D   A   I   N   E   A   F   E

900       GCCGTCGTTCTGTGGCTATGCCAACTCGGCTACGCCAACTCCCTGATGCCACAGAGACTTCCCCACGGCATACCAA
 279       A   V   V   L   W   L   G   Y   A   N   S   A   L   N   P   I   L   Y   A   T   L   N   R   D   F   R   T   A   Y   Q

1000       CAGCTCTTCCGCTGCAGGCCGGCCAGCCACAATGCCAGGAAACTTCTCGAGGTCGAACAGCTCTCAGCTGGCCAGGAATCAAAGCCGA
 310       Q   L   F   R   C   R   P   A   S   H   N   A   Q   E   T   S   L   R   S   N   S   S   Q   L   A   R   N   Q   S   R

1100       GAACCCATGCGGCAGGAAGAGAAGCCCCTGAAGCTCCAGGTGTGGAGTGGGACAGAGGTCACAGCCCCTCGAGGAGCCACAGACAGGTAA
 341       E   P   M   R   Q   E   E   K   P   L   K   L   Q   V   W   S   G   T   E   V   T   A   P   R   G   A   T   D   R   -

1200       TTGCCCTGACCATTTGTGTACCAGACAAGCGCTGGGAGGGGGGTGTCCCACTAGTGACCACCATTAAGGGGATGGCTGTTCCCCAGG
1300       AGCTAGTTGAACATTCTGTGCTGGGAAGTTTCATGGAAGTTTCATGAGCACTTCCAAACCTCATGTGTTCCATCCTCCCAATGGCCTCCT
```

FIG. 2B

```
                                                                        I
CANH2     -  MISNGTGSSFCLDSPPCRITVS------------------VV-LTVLI------LITIAGNVVVCLAVGLNRRLRSLT
HAMADRB2  -  MGPPGNDSDFLLTTNGSHVPDHDVTEERDEAWVGAILMSVIVLAIVGGF------GNVLVITAIAKFERLQTVT
HUMADB3   -  -MAPWPHENSSLAPWPDLPTLAPNTANTS-GLPGVPWEAALAGALLALAVLATV-------NLLVIVAIAWTPRLQINT
BOVSUBK   -  MGACVVMTDINISS-GLDSNATGI---TAFSMPGWQLALWTAAY----LAL-VLVAVM-------GNATVIWIILAHQRMRTVT
HUMACHRM2 -  MFVNFILFPCRFKCLFATWLLIRERKMNNSTNSSNNSLALTSPYKTFEVVFI-VLVAGSLSLVTIIGNILVMVSIKVNRHLQTVN
RATDDP2   -  MDPLNLSWYDDDLERQNWSRPFNGSEGKADRPHYNYYAMLLTLLIFIIVFGN-VLVCM-----------AVSREKALQTIT

II                                             III
CANH2     -  NCFIVSLAITDLLLGLLVLPFSAFYQLSCRWSFGKVFCNIYTSLDVMLC-TA---SILNLFMISLDRYCA-VTDP-LRYPVLITP
HAMADRB2  -  NYFITSLACADLVMGLAVVPFGASHILMKMWNFGNFWCEFWTSIDV-LCVTA---SIETLCVIAVDRYIAITSPFKYQS--LLIK
HUMADB3   -  NVFVTSLAAADLVMGLLVMPPAATLALTGHWPLGATGCELWTSVDV-LCVTA---SIETLCALAVDRYLA-VTNT-LRYGALVTK
BOVSUBK   -  NYFIVNLALADLCMAAFNAAFNFVYASHNIWYFGRAFCYFQNLFPI----TAMFVSIYSMTAIAADRYMAIVHPFQPR---LSAP
HUMACHRM2 -  NYLFSLACADLIIGVFSMNLYTLYTVIGYWPLGPVVCDLWLALDYVVS-NASVMNLLIISF---DRYFC-VTKP-LTYPVKRTT
RATDDP2   -  NYLIVSLAVADLLVATILVMPWVVYLEVVGEWKFSRIHCDIFVTLDVMMC-TA---SILNLCAISIDRYTA-VAMPMLYNTRYSSK

IV                                                 V
CANH2     -  V--RVAV---SLVLIWISITLSFLSIHLGWNSR-NETSSFNHTIPKCKVQV------NLVYGL-VDGLVTFYLP----LLVM
HAMADRB2  -  NKARM-V-ILM---VWIVSGLTSFLPIQMHWY-RATHQKAID-----CYHKET-CCDFFTNQAY-AIASSIVSFYVP----LVVM
HUMADB3   -  RCARTAV---VLVWVSAAVSFAPIMSQWW-RVGA---DAEAQRCHSNPR-CCAFASNMPYVL-LSSSVSFYLP----LLVM
BOVSUBK   -  GT-R-AV-IAGIWLVALALAFPQCFYSTITT--------DEGATKCVVAWPEDSGGKMLLLYHLIVIALIYF-LP----LVVM
HUMACHRM2 -  KMAGMM--IA---AAWVLSFILWAPAILF-WQFIVGVRTVEDGE-----CYIQFFS-----NAAVTFGT-AIAAFYLP----VIIM
RATDDP2   -  R--RVTVMIAI---VWVLSFTISCPLLFGLNNTDQNE-----------CIIANPAFVVY--------SSIVSFYVPFIVTLLVY
```

FIG. 3A

```
CANH2      -- CITYYRIFKIARDQ-------AKRIHMGSWKAATIG------------------------------------EEKATV
HAMADRB2   -- VFVYSRVFQVEGRFHSPNL---AKRQLQKIDKSGQVEQDGRSGHGLRRSSKFCLK---------------------EEKALK
HUMADB3    -- LFVYARVFVV-----------ATRQLRLLRGELGRFPPEESPAPPSRSLAPAPVGTCAPPEGVPACGRRPARLLPLR--EERALC
BOVSUBK    -- FVAYSVIGLTLWRR-----------------------------------------SVPGHQAHGANLRHLQAKKKFVK
HUMACHRM2  -- T-VLYWHISV--137 aa---ARKIVKMTKQPAKKKPPPSR----------------------------------EKKVTR
RATD0P2    -- IKIYIVLRKRPKRVNTKRSSRAFRANLKT-----72 aa------FFEIQTMPNGKTRTSLKTMSRRKL-SQQKEKKATQ

VI                                              VII
CANH2      -- TLAAVMGAFIICWFPYFTVFVYRGLKGDDAIWE-AFEAV--VL-WLGYANSALNPILYATLNRDFRTAYQ-QL-FRCRPASHNAQ
HAMADRB2   -- TLGIIMGTFTLCWLPFFIVNIVHVIQDNLIPKEVYI----L-LNWLGYVNSAFNPLIYCRS-PDFRIAFQELL----CLRRSSSKA
HUMADB3    -- TLGLIMGTFTLCWLPFFLANVLRALGGPSLVPGPAF-----LALNWLGYANSAFNPLIYCRS-PDFRSAFRRLL-CRCGRRLPPEP
BOVSUBK    -- TMVLVVVFAICWLPYHLYFILGTFQ-EDIYCHKFIQQVYLALFWLAMSSTMYNPIYCCLNHRFRSGFR--LAFRCCPWVTPTE
HUMACHRM2  -- TILAILLAFIIITWAPYN-VMVLINTFCAPCIPNTVWTIGY-----WLCYINSTINPACYALCNATFKKTFKHLLM--CHYKNIGATR
RATD0P2    -- MLAIVLGVFIICWLPFFITHILNIHCDCNIHQSSTAPSH----------GWAMSTVPSTPSSTPPSTSSSARPS

CANH2      -- ET-------SLRSNSSQLA-RNQSREPMRQEEKPLK-LQVWSGTEVTAPRGATDR
HAMADRB2   -- YGNGY---SSNSNGKTDYMGEASGCQLGQ-EKESERLCEDPPGTESFVNCQGTVPSLSLDSQGRNCSTNDSPL
HUMADB3    -- CAAARPALFPSGVPAARSSPAQPRLCQRLDG
BOVSUBK    -- EDKMELTYTPSLSTRVNRCHTKEIFFMSGDVAPSEAVNGQAESPQAGVSTEP
```

*FIG. 3B*

THIRD TRANSMEMBRANE DOMAIN
```
                        *
HUMH2     - CNIYT-SLD-VMLV-TA---SILNLFMMRLDRY
CANH2     - CNIYT-SLD-VMLC-TA---SILNLFMISLDRY
HUMADA2   - DGVYL-ALD-VLFC-TS---SIVHLCAISLDRY
HUMADRB1  - CELWT-SVD-V-LCVTA---SIETLCVIALDRY
HAMADRB2  - CEFWT-SID-V-LCVTA---SIETLCVIAVDRY
HUMADB3   - CELWT-SVD-V-LCVTA---SIETLCALAVDRY
RATDOP2   - CDIFVT-LD-VMMC-TA---SILNLCAISIDRY
HUMACHRM2 - CDLWLA-LDYVVSN--A---SVMNLLIISFDRY
RATSUBP   - CKFHNFFPIAALF---A---SIYSMTAVAFDRY
BOVSUBK   - CYFQNLFPI------TAMFVSIYSMTAIAADRY
MAS       - YTIVTLS---VTFLFGYNTGL--LLTAISVERC
```

FIG. 4A

FIFTH TRANSMEMBRANE DOMAIN
```
                       * *
HUMH2     - NEVYGL-VDGLVTFYLP----LLIMCITY
CANH2     - NLVYGL-VDGLVTFYLP----LLVMCITY
HUMADRB1  - NRAYAI-ASSVVSFYVP----LCIMAFVY
HAMADRB2  - NQAYAI-ASSIVSFYVP----LVVMVFVY
HUMADB3   - NMPYVL-LSSSVSFYLP----LLVMLFVY
HAMADRA1  - EPFYAL-FSSLGSFYIPLAV-ILVMYC
RATDOP2   - NPAFVV-YSSIVSFYVPFIVTLLVYIKIY
BOVSUBK   - LLLYHLIVIALIYF-LP----LVVM-FVA
RATSUBP   - EKAYHICVTVLIYF-LP----LLV--IGY
HUMACHRM2 - NAAVTFGTAIAA-FYLP----VIIMT-VL
MAS       - DCRAVIIFIAILSF-LVFTPLMLVSSTIL
```

FIG. 4B 5,885,824

SEQUENCE LISTING ( 1 ) GENERAL INFORMATION:

( i i i ) NUMBER OF SEQUENCES: 41

( 2 ) INFORMATION FOR SEQ ID NO:1:

( i ) SEQUENCE CHARACTERISTICS:
        ( A ) LENGTH: 1080 base pairs
        ( B ) TYPE: nucleic acid
        ( C ) STRANDEDNESS: unknown
        ( D ) TOPOLOGY: unknown ( i i ) MOLECULE TYPE: DNA (genomic)

( v i ) ORIGINAL SOURCE:
        ( A ) ORGANISM: Homo sapiens
        ( F ) TISSUE TYPE: Stomach mucosa ( i x ) FEATURE:
        ( A ) NAME/KEY: CDS
        ( B ) LOCATION: 1..1080

( x i ) SEQUENCE DESCRIPTION: SEQ ID NO:1:

```
ATG  GCA  CCC  AAT  GGC  ACA  GCC  TCT  TCC  TTT  TGC  CTG  GAC  TCT  ACC  GCA       48
Met  Ala  Pro  Asn  Gly  Thr  Ala  Ser  Ser  Phe  Cys  Leu  Asp  Ser  Thr  Ala
 1                    5                        10                       15

TGC  AAG  ATC  ACC  ATC  ACC  GTG  GTC  CTT  GCG  GTC  CTC  ATC  CTC  ATC  ACC       96
Cys  Lys  Ile  Thr  Ile  Thr  Val  Val  Leu  Ala  Val  Leu  Ile  Leu  Ile  Thr
```

-continued

```
                     20                              25                              30
GTT  GCT  GGC  AAT  GTG  GTC  GTC  TGT  CTG  GCC  GTG  GGC  TTG  AAC  CGC  CGG        144
Val  Ala  Gly  Asn  Val  Val  Val  Cys  Leu  Ala  Val  Gly  Leu  Asn  Arg  Arg
               35                         40                         45

CTC  CGC  AAC  CTG  ACC  AAT  TGT  TTC  ATC  GTG  TCC  TTG  GCT  ATC  ACT  GAC        192
Leu  Arg  Asn  Leu  Thr  Asn  Cys  Phe  Ile  Val  Ser  Leu  Ala  Ile  Thr  Asp
     50                         55                         60

CTG  CTC  CTC  GGC  CTC  CTG  GTG  CTC  CCC  TTC  TCT  GCC  ATC  TAC  CAG  CTG        240
Leu  Leu  Leu  Gly  Leu  Leu  Val  Leu  Pro  Phe  Ser  Ala  Ile  Tyr  Gln  Leu
65                       70                         75                         80

TCC  TGC  AAG  TGG  AGC  TTT  GGC  AAG  GTC  TTC  TGC  AAT  ATC  TAC  ACC  AGC        288
Ser  Cys  Lys  Trp  Ser  Phe  Gly  Lys  Val  Phe  Cys  Asn  Ile  Tyr  Thr  Ser
                    85                         90                         95

CTG  GAT  GTG  ATG  CTC  TGC  ACA  GCC  TCC  ATT  CTT  AAC  CTC  TTC  ATG  ATC        336
Leu  Asp  Val  Met  Leu  Cys  Thr  Ala  Ser  Ile  Leu  Asn  Leu  Phe  Met  Ile
               100                        105                        110

AGC  CTC  GAC  CGG  TAC  TGC  GCT  GTC  ATG  GAC  CCA  CTG  CGG  TAC  CCT  GTG        384
Ser  Leu  Asp  Arg  Tyr  Cys  Ala  Val  Met  Asp  Pro  Leu  Arg  Tyr  Pro  Val
          115                        120                        125

CTG  GTC  ACC  CCA  GTT  CGG  GTC  GCC  ATC  TCT  CTG  GTC  TTA  ATT  TGG  GTC        432
Leu  Val  Thr  Pro  Val  Arg  Val  Ala  Ile  Ser  Leu  Val  Leu  Ile  Trp  Val
130                      135                        140

ATC  TCC  ATT  ACC  CTG  TCC  TTT  CTG  TCT  ATC  CAC  CTG  GGG  TGG  AAC  AGC        480
Ile  Ser  Ile  Thr  Leu  Ser  Phe  Leu  Ser  Ile  His  Leu  Gly  Trp  Asn  Ser
145                      150                        155                        160

AGG  AAC  GAG  ACC  AGC  AAG  GGC  AAT  CAT  ACC  ACC  TCT  AAG  TGC  AAA  GTC        528
Arg  Asn  Glu  Thr  Ser  Lys  Gly  Asn  His  Thr  Thr  Ser  Lys  Cys  Lys  Val
                    165                        170                        175

CAG  GTC  AAT  GAA  GTG  TAC  GGG  CTG  GTG  GAT  GGG  CTG  GTC  ACC  TTC  TAC        576
Gln  Val  Asn  Glu  Val  Tyr  Gly  Leu  Val  Asp  Gly  Leu  Val  Thr  Phe  Tyr
               180                        185                        190

CTC  CCG  CTA  CTG  ATC  ATG  TGC  ATC  ACC  TAC  TAC  CGC  ATC  TTC  AAG  GTC        624
Leu  Pro  Leu  Leu  Ile  Met  Cys  Ile  Thr  Tyr  Tyr  Arg  Ile  Phe  Lys  Val
          195                        200                        205

GCC  CGG  GAT  CAG  GCC  AAG  AGG  ATC  AAT  CAC  ATT  AGC  TCC  TGG  AAG  GCA        672
Ala  Arg  Asp  Gln  Ala  Lys  Arg  Ile  Asn  His  Ile  Ser  Ser  Trp  Lys  Ala
210                      215                        220

GCC  ACC  ATC  AGG  GAG  CAC  AAA  GCC  ACA  GTG  ACA  CTG  GCC  GCC  GTC  ATG        720
Ala  Thr  Ile  Arg  Glu  His  Lys  Ala  Thr  Val  Thr  Leu  Ala  Ala  Val  Met
225                      230                        235                        240

GGG  GCC  TTC  ATC  ATC  TGC  TGG  TTT  CCC  TAC  TTC  ACC  GCG  TTT  GTG  TAC        768
Gly  Ala  Phe  Ile  Ile  Cys  Trp  Phe  Pro  Tyr  Phe  Thr  Ala  Phe  Val  Tyr
                    245                        250                        255

CGT  GGG  CTG  AGA  GGG  GAT  GAT  GCC  ATC  AAT  GAG  GTG  TTA  GAA  GCC  ATC        816
Arg  Gly  Leu  Arg  Gly  Asp  Asp  Ala  Ile  Asn  Glu  Val  Leu  Glu  Ala  Ile
               260                        265                        270

GTT  CTG  TGG  CTG  GGC  TAT  GCC  AAC  TCA  GCC  CTG  AAC  CCC  ATC  CTG  TAT        864
Val  Leu  Trp  Leu  Gly  Tyr  Ala  Asn  Ser  Ala  Leu  Asn  Pro  Ile  Leu  Tyr
          275                        280                        285

GCT  GCG  CTG  AAC  AGA  GAC  TTC  CGC  ACC  GGG  TAC  CAA  CAG  CTC  TTC  TGC        912
Ala  Ala  Leu  Asn  Arg  Asp  Phe  Arg  Thr  Gly  Tyr  Gln  Gln  Leu  Phe  Cys
290                      295                        300

TGC  AGG  CTG  GCC  AAC  CGC  AAC  TCC  CAC  AAA  ACT  TCT  CTG  AGG  TCC  AAC        960
Cys  Arg  Leu  Ala  Asn  Arg  Asn  Ser  His  Lys  Thr  Ser  Leu  Arg  Ser  Asn
305                      310                        315                        320

GCC  TCT  CAG  CTG  TCC  AGG  ACC  CAA  AGC  CGA  GAA  CCC  AGG  CAA  CAG  GAA       1008
Ala  Ser  Gln  Leu  Ser  Arg  Thr  Gln  Ser  Arg  Glu  Pro  Arg  Gln  Gln  Glu
                    325                        330                        335

GAG  AAA  CCC  CTG  AAG  CTC  CAG  GTG  TGG  AGT  GGG  ACA  GAA  GTC  ACG  GCC       1056
Glu  Lys  Pro  Leu  Lys  Leu  Gln  Val  Trp  Ser  Gly  Thr  Glu  Val  Thr  Ala
```

```
                    340                      345                      350
CCC  CAG  GGA  GCC  ACA  GAC  AGG  TAA                                              1080
Pro  Gln  Gly  Ala  Thr  Asp  Arg
          355
```

( 2 ) INFORMATION FOR SEQ ID NO:2:

( i ) SEQUENCE CHARACTERISTICS:
        ( A ) LENGTH: 359 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Ala  Pro  Asn  Gly  Thr  Ala  Ser  Ser  Phe  Cys  Leu  Asp  Ser  Thr  Ala
  1              5                        10                       15
Cys  Lys  Ile  Thr  Ile  Thr  Val  Val  Leu  Ala  Val  Leu  Ile  Leu  Ile  Thr
              20                       25                       30
Val  Ala  Gly  Asn  Val  Val  Val  Cys  Leu  Ala  Val  Gly  Leu  Asn  Arg  Arg
              35                       40                       45
Leu  Arg  Asn  Leu  Thr  Asn  Cys  Phe  Ile  Val  Ser  Leu  Ala  Ile  Thr  Asp
      50                        55                       60
Leu  Leu  Leu  Gly  Leu  Leu  Val  Leu  Pro  Phe  Ser  Ala  Ile  Tyr  Gln  Leu
 65                       70                       75                       80
Ser  Cys  Lys  Trp  Ser  Phe  Gly  Lys  Val  Phe  Cys  Asn  Ile  Tyr  Thr  Ser
                    85                       90                       95
Leu  Asp  Val  Met  Leu  Cys  Thr  Ala  Ser  Ile  Leu  Asn  Leu  Phe  Met  Ile
                  100                      105                      110
Ser  Leu  Asp  Arg  Tyr  Cys  Ala  Val  Met  Asp  Pro  Leu  Arg  Tyr  Pro  Val
              115                      120                      125
Leu  Val  Thr  Pro  Val  Arg  Val  Ala  Ile  Ser  Leu  Val  Leu  Ile  Trp  Val
        130                      135                      140
Ile  Ser  Ile  Thr  Leu  Ser  Phe  Leu  Ser  Ile  His  Leu  Gly  Trp  Asn  Ser
145                      150                      155                      160
Arg  Asn  Glu  Thr  Ser  Lys  Gly  Asn  His  Thr  Thr  Ser  Lys  Cys  Lys  Val
                   165                      170                      175
Gln  Val  Asn  Glu  Val  Tyr  Gly  Leu  Val  Asp  Gly  Leu  Val  Thr  Phe  Tyr
              180                      185                      190
Leu  Pro  Leu  Leu  Ile  Met  Cys  Ile  Thr  Tyr  Tyr  Arg  Ile  Phe  Lys  Val
        195                      200                      205
Ala  Arg  Asp  Gln  Ala  Lys  Arg  Ile  Asn  His  Ile  Ser  Ser  Trp  Lys  Ala
     210                      215                      220
Ala  Thr  Ile  Arg  Glu  His  Lys  Ala  Thr  Val  Thr  Leu  Ala  Ala  Val  Met
225                      230                      235                      240
Gly  Ala  Phe  Ile  Ile  Cys  Trp  Phe  Pro  Tyr  Phe  Thr  Ala  Phe  Val  Tyr
                   245                      250                      255
Arg  Gly  Leu  Arg  Gly  Asp  Asp  Ala  Ile  Asn  Glu  Val  Leu  Glu  Ala  Ile
              260                      265                      270
Val  Leu  Trp  Leu  Gly  Tyr  Ala  Asn  Ser  Ala  Leu  Asn  Pro  Ile  Leu  Tyr
        275                      280                      285
Ala  Ala  Leu  Asn  Arg  Asp  Phe  Arg  Thr  Gly  Tyr  Gln  Gln  Leu  Phe  Cys
     290                      295                      300
Cys  Arg  Leu  Ala  Asn  Arg  Asn  Ser  His  Lys  Thr  Ser  Leu  Arg  Ser  Asn
305                      310                      315                      320
Ala  Ser  Gln  Leu  Ser  Arg  Thr  Gln  Ser  Arg  Glu  Pro  Arg  Gln  Gln  Glu
                   325                      330                      335
```

| Glu | Lys | Pro | Leu | Lys | Leu | Gln | Val | Trp | Ser | Gly | Thr | Glu | Val | Thr | Ala |
||||340|||||345||||350|||

| Pro | Gln | Gly | Ala | Thr | Asp | Arg |
|||355|||||

( 2 ) INFORMATION FOR SEQ ID NO:3:

( i ) SEQUENCE CHARACTERISTICS:
        ( A ) LENGTH: 1080 base pairs
        ( B ) TYPE: nucleic acid
        ( C ) STRANDEDNESS: unknown
        ( D ) TOPOLOGY: unknown ( i i ) MOLECULE TYPE: DNA (genomic)

( v i ) ORIGINAL SOURCE:
        ( A ) ORGANISM: Dog
        ( F ) TISSUE TYPE: stomach
        ( G ) CELL TYPE: parietal ( v i i ) IMMEDIATE SOURCE:
        ( A ) LIBRARY: canine ( i x ) FEATURE:
        ( A ) NAME/KEY: CDS
        ( B ) LOCATION: 1..1080

( x i ) SEQUENCE DESCRIPTION: SEQ ID NO:3:

| ATG | ATA | TCT | AAC | GGC | ACA | GGC | TCT | TCC | TTT | TGT | CTG | GAC | TCT | CCT | CCA | 48 |
| Met | Ile | Ser | Asn | Gly | Thr | Gly | Ser | Ser | Phe | Cys | Leu | Asp | Ser | Pro | Pro | |
| 1 | | | | 5 | | | | | 10 | | | | | 15 | | |

| TGC | AGG | ATC | ACT | GTC | AGC | GTG | GTC | CTC | ACT | GTC | CTC | ATC | CTC | ATC | ACC | 96 |
| Cys | Arg | Ile | Thr | Val | Ser | Val | Val | Leu | Thr | Val | Leu | Ile | Leu | Ile | Thr | |
| | | | 20 | | | | | 25 | | | | | 30 | | | |

| ATC | GCC | GGC | AAT | GTG | GTG | GTC | TGC | CTG | GCT | GTG | GGC | CTG | AAC | CGC | CGG | 144 |
| Ile | Ala | Gly | Asn | Val | Val | Val | Cys | Leu | Ala | Val | Gly | Leu | Asn | Arg | Arg | |
| | | | 35 | | | | 40 | | | | | 45 | | | | |

| CTC | CGC | AGT | CTG | ACT | AAC | TGC | TTC | ATT | GTG | TCG | TTG | GCT | ATC | ACC | GAT | 192 |
| Leu | Arg | Ser | Leu | Thr | Asn | Cys | Phe | Ile | Val | Ser | Leu | Ala | Ile | Thr | Asp | |
| | 50 | | | | | 55 | | | | | 60 | | | | | |

| CTG | CTC | CTC | GGC | CTC | CTG | GTG | CTG | CCC | TTC | TCG | GCC | TTC | TAC | CAG | CTA | 240 |
| Leu | Leu | Leu | Gly | Leu | Leu | Val | Leu | Pro | Phe | Ser | Ala | Phe | Tyr | Gln | Leu | |
| 65 | | | | | 70 | | | | | 75 | | | | | 80 | |

| TCC | TGC | AGG | TGG | AGC | TTC | GGC | AAA | GTC | TTC | TGC | AAT | ATC | TAT | ACC | AGC | 288 |
| Ser | Cys | Arg | Trp | Ser | Phe | Gly | Lys | Val | Phe | Cys | Asn | Ile | Tyr | Thr | Ser | |
| | | | | 85 | | | | | 90 | | | | | 95 | | |

| TTG | GAT | GTG | ATG | CTG | TGC | ACG | GCC | TCC | ATC | CTC | AAC | CTC | TTC | ATG | ATC | 336 |
| Leu | Asp | Val | Met | Leu | Cys | Thr | Ala | Ser | Ile | Leu | Asn | Leu | Phe | Met | Ile | |
| | | | 100 | | | | | 105 | | | | | 110 | | | |

| AGC | CTT | GAC | CGG | TAC | TGC | GCT | GTC | ACT | GAC | CCC | CTG | CGC | TAC | CCT | GTG | 384 |
| Ser | Leu | Asp | Arg | Tyr | Cys | Ala | Val | Thr | Asp | Pro | Leu | Arg | Tyr | Pro | Val | |
| | | 115 | | | | | 120 | | | | | 125 | | | | |

| CTT | ATC | ACC | CCA | GTC | CGG | GTC | GCC | GTC | TCT | CTT | GTC | TTA | ATT | TGG | GTC | 432 |
| Leu | Ile | Thr | Pro | Val | Arg | Val | Ala | Val | Ser | Leu | Val | Leu | Ile | Trp | Val | |
| | 130 | | | | | 135 | | | | | 140 | | | | | |

| ATC | TCC | ATC | ACC | CTG | TCC | TTC | CTG | TCT | ATT | CAT | CTG | GGG | TGG | AAC | AGC | 480 |
| Ile | Ser | Ile | Thr | Leu | Ser | Phe | Leu | Ser | Ile | His | Leu | Gly | Trp | Asn | Ser | |
| 145 | | | | | 150 | | | | | 155 | | | | | 160 | |

| AGG | AAT | GAG | ACC | AGC | AGT | TTC | AAT | CAC | ACC | ATT | CCC | AAG | TGC | AAA | GTC | 528 |
| Arg | Asn | Glu | Thr | Ser | Ser | Phe | Asn | His | Thr | Ile | Pro | Lys | Cys | Lys | Val | |
| | | | | 165 | | | | | 170 | | | | | 175 | | |

| CAG | GTC | AAC | TTG | GTG | TAT | GGC | TTG | GTG | GAT | GGG | CTG | GTC | ACC | TTC | TAC | 576 |
| Gln | Val | Asn | Leu | Val | Tyr | Gly | Leu | Val | Asp | Gly | Leu | Val | Thr | Phe | Tyr | |
| | | | 180 | | | | | 185 | | | | | 190 | | | |

| | | | | | | | | | | | | | | | | |
|---|---|---|---|---|---|---|---|---|---|---|---|---|---|---|---|---|
| CTG | CCG | CTG | CTG | GTC | ATG | TGC | ATC | ACC | TAC | TAC | CGC | ATC | TTC | AAG | ATT | 624 |
| Leu | Pro | Leu | Leu | Val | Met | Cys | Ile | Thr | Tyr | Tyr | Arg | Ile | Phe | Lys | Ile | |
| | | 195 | | | | | 200 | | | | | 205 | | | | |
| GCC | CGG | AGG | ATC | CAT | GAC | CAG | GCC | AAG | CAC | ATG | GGC | TCC | TGG | AAG | GCA | 672 |
| Ala | Arg | Arg | Ile | His | Asp | Gln | Ala | Lys | His | Met | Gly | Ser | Trp | Lys | Ala | |
| 210 | | | | | | 215 | | | | | 220 | | | | | |
| GCT | ACC | ATT | GGG | GAG | CAC | AAA | GCC | ACA | GTG | ACA | CTG | GCT | GCA | GTG | ATG | 720 |
| Ala | Thr | Ile | Gly | Glu | His | Lys | Ala | Thr | Val | Thr | Leu | Ala | Ala | Val | Met | |
| 225 | | | | | 230 | | | | | 235 | | | | | 240 | |
| GGA | GCC | TTC | ATC | ATA | TGC | TGG | TTC | CCC | TAC | TTT | ACT | GTG | TTT | GTT | TAC | 768 |
| Gly | Ala | Phe | Ile | Ile | Cys | Trp | Phe | Pro | Tyr | Phe | Thr | Val | Phe | Val | Tyr | |
| | | | | 245 | | | | | 250 | | | | | 255 | | |
| CGT | GGG | CTG | AAA | GGG | GAT | GAT | GCC | ATC | AAT | GAG | GCT | TTT | GAA | GCC | GTC | 816 |
| Arg | Gly | Leu | Lys | Gly | Asp | Asp | Ala | Ile | Asn | Glu | Ala | Phe | Glu | Ala | Val | |
| | | | 260 | | | | | 265 | | | | | 270 | | | |
| GTT | CTG | TGG | CTG | GGC | TAT | GCC | AAC | TCG | GCC | CTG | AAC | CCT | ATC | CTG | TAT | 864 |
| Val | Leu | Trp | Leu | Gly | Tyr | Ala | Asn | Ser | Ala | Leu | Asn | Pro | Ile | Leu | Tyr | |
| | | 275 | | | | | 280 | | | | | 285 | | | | |
| GCC | ACA | CTG | AAC | AGA | GAC | TTC | CGC | ACG | GCA | TAC | CAA | CAG | CTC | TTC | CGC | 912 |
| Ala | Thr | Leu | Asn | Arg | Asp | Phe | Arg | Thr | Ala | Tyr | Gln | Gln | Leu | Phe | Arg | |
| | 290 | | | | | 295 | | | | | 300 | | | | | |
| TGC | AGG | CCG | GCC | AGC | CAC | AAT | GCC | CAG | GAA | ACT | TCT | CTG | AGG | TCG | AAC | 960 |
| Cys | Arg | Pro | Ala | Ser | His | Asn | Ala | Gln | Glu | Thr | Ser | Leu | Arg | Ser | Asn | |
| 305 | | | | | 310 | | | | | 315 | | | | | 320 | |
| AGC | TCT | CAG | CTG | GCC | AGG | AAT | CAA | AGC | CGA | GAA | CCC | ATG | CGG | CAG | GAA | 1008 |
| Ser | Ser | Gln | Leu | Ala | Arg | Asn | Gln | Ser | Arg | Glu | Pro | Met | Arg | Gln | Glu | |
| | | | | 325 | | | | | 330 | | | | | 335 | | |
| GAG | AAG | CCC | CTG | AAG | CTC | CAG | GTG | TGG | AGT | GGG | ACA | GAG | GTC | ACA | GCC | 1056 |
| Glu | Lys | Pro | Leu | Lys | Leu | Gln | Val | Trp | Ser | Gly | Thr | Glu | Val | Thr | Ala | |
| | | | 340 | | | | | 345 | | | | | 350 | | | |
| CCT | CGA | GGA | GCC | ACA | GAC | AGG | TAA | | | | | | | | | 1080 |
| Pro | Arg | Gly | Ala | Thr | Asp | Arg | | | | | | | | | | |
| | | 355 | | | | | | | | | | | | | | |

( 2 ) INFORMATION FOR SEQ ID NO:4:

( i ) SEQUENCE CHARACTERISTICS:
        ( A ) LENGTH: 359 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| | | | | | | | | | | | | | | |
|---|---|---|---|---|---|---|---|---|---|---|---|---|---|---|
| Met | Ile | Ser | Asn | Gly | Thr | Gly | Ser | Ser | Phe | Cys | Leu | Asp | Ser | Pro | Pro |
| 1 | | | | 5 | | | | | 10 | | | | | 15 | |
| Cys | Arg | Ile | Thr | Val | Ser | Val | Val | Leu | Thr | Val | Leu | Ile | Leu | Ile | Thr |
| | | | 20 | | | | | 25 | | | | | 30 | | |
| Ile | Ala | Gly | Asn | Val | Val | Val | Cys | Leu | Ala | Val | Gly | Leu | Asn | Arg | Arg |
| | | | 35 | | | | 40 | | | | | 45 | | | |
| Leu | Arg | Ser | Leu | Thr | Asn | Cys | Phe | Ile | Val | Ser | Leu | Ala | Ile | Thr | Asp |
| | | 50 | | | | | 55 | | | | | 60 | | | |
| Leu | Leu | Leu | Gly | Leu | Leu | Val | Leu | Pro | Phe | Ser | Ala | Phe | Tyr | Gln | Leu |
| 65 | | | | | 70 | | | | | 75 | | | | | 80 |
| Ser | Cys | Arg | Trp | Ser | Phe | Gly | Lys | Val | Phe | Cys | Asn | Ile | Tyr | Thr | Ser |
| | | | | 85 | | | | | 90 | | | | | 95 | |
| Leu | Asp | Val | Met | Leu | Cys | Thr | Ala | Ser | Ile | Leu | Asn | Leu | Phe | Met | Ile |
| | | | 100 | | | | | 105 | | | | | 110 | | |
| Ser | Leu | Asp | Arg | Tyr | Cys | Ala | Val | Thr | Asp | Pro | Leu | Arg | Tyr | Pro | Val |
| | | 115 | | | | | 120 | | | | | 125 | | | |

```
Leu  Ile  Thr  Pro  Val  Arg  Val  Ala  Val  Ser  Leu  Val  Leu  Ile  Trp  Val
     130                 135                 140

Ile  Ser  Ile  Thr  Leu  Ser  Phe  Leu  Ser  Ile  His  Leu  Gly  Trp  Asn  Ser
145                      150                 155                           160

Arg  Asn  Glu  Thr  Ser  Ser  Phe  Asn  His  Thr  Ile  Pro  Lys  Cys  Lys  Val
                    165                 170                      175

Gln  Val  Asn  Leu  Val  Tyr  Gly  Leu  Val  Asp  Gly  Leu  Val  Thr  Phe  Tyr
               180                 185                      190

Leu  Pro  Leu  Leu  Val  Met  Cys  Ile  Thr  Tyr  Tyr  Arg  Ile  Phe  Lys  Ile
          195                 200                      205

Ala  Arg  Arg  Ile  His  Asp  Gln  Ala  Lys  His  Met  Gly  Ser  Trp  Lys  Ala
     210                 215                      220

Ala  Thr  Ile  Gly  Glu  His  Lys  Ala  Thr  Val  Thr  Leu  Ala  Ala  Val  Met
225                      230                 235                           240

Gly  Ala  Phe  Ile  Ile  Cys  Trp  Phe  Pro  Tyr  Phe  Thr  Val  Phe  Val  Tyr
               245                      250                      255

Arg  Gly  Leu  Lys  Gly  Asp  Asp  Ala  Ile  Asn  Glu  Ala  Phe  Glu  Ala  Val
          260                      265                      270

Val  Leu  Trp  Leu  Gly  Tyr  Ala  Asn  Ser  Ala  Leu  Asn  Pro  Ile  Leu  Tyr
          275                 280                      285

Ala  Thr  Leu  Asn  Arg  Asp  Phe  Arg  Thr  Ala  Tyr  Gln  Gln  Leu  Phe  Arg
     290                      295                 300

Cys  Arg  Pro  Ala  Ser  His  Asn  Ala  Gln  Glu  Thr  Ser  Leu  Arg  Ser  Asn
305                      310                 315                           320

Ser  Ser  Gln  Leu  Ala  Arg  Asn  Gln  Ser  Arg  Glu  Pro  Met  Arg  Gln  Glu
                    325                      330                      335

Glu  Lys  Pro  Leu  Lys  Leu  Gln  Val  Trp  Ser  Gly  Thr  Glu  Val  Thr  Ala
               340                      345                      350

Pro  Arg  Gly  Ala  Thr  Asp  Arg
          355
```

( 2 ) INFORMATION FOR SEQ ID NO:5:

( i ) SEQUENCE CHARACTERISTICS:
    ( A ) LENGTH: 1419 base pairs
    ( B ) TYPE: nucleic acid
    ( C ) STRANDEDNESS: unknown
    ( D ) TOPOLOGY: unknown ( i i ) MOLECULE TYPE: DNA (genomic)

( v i ) ORIGINAL SOURCE:
    ( A ) ORGANISM: Dog
    ( F ) TISSUE TYPE: stomach
    ( G ) CELL TYPE: parietal ( v i i ) IMMEDIATE SOURCE:
    ( A ) LIBRARY: canine ( i x ) FEATURE:
    ( A ) NAME/KEY: CDS
    ( B ) LOCATION: 168..1244

( x i ) SEQUENCE DESCRIPTION: SEQ ID NO:5:

```
CTAGAAAAAC  AGTCGTCGGG  CAGTTATTGT  AACCTCCCCA  CGTCTGGACA  TTTTCTTTTG        60

GCTCCATTAG  GAGCCTAGAG  CCCAGCGGTT  GACATCATTG  ACACACTGGG  GAGCTGGATG       120

AGAAGTCCAG  GGGCTGTGGG  CAGAGGCCAG  AGCCGTAGGA  TCCCAGG ATG ATA TCT          176
                                                        Met Ile Ser
                                                          1

AAC GGC ACA GGC TCT TCC TTT TGT CTG GAC TCT CCT CCA TGC AGG ATC             224
Asn Gly Thr Gly Ser Ser Phe Cys Leu Asp Ser Pro Pro Cys Arg Ile
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     | 5   |     |     |     |     | 10  |     |     |     |     | 15  |     |     |      |
| ACT | GTC | AGC | GTG | GTC | CTC | ACT | GTC | CTC | ATC | CTC | ATC | ACC | ATC | GCC | GGC | 272  |
| Thr | Val | Ser | Val | Val | Leu | Thr | Val | Leu | Ile | Leu | Ile | Thr | Ile | Ala | Gly |      |
| 20  |     |     |     |     | 25  |     |     |     |     | 30  |     |     |     |     | 35  |      |
| AAT | GTG | GTG | GTC | TGC | CTG | GCT | GTG | GGC | CTG | AAC | CGC | CGG | CTC | CGC | AGT | 320  |
| Asn | Val | Val | Val | Cys | Leu | Ala | Val | Gly | Leu | Asn | Arg | Arg | Leu | Arg | Ser |      |
|     |     |     |     | 40  |     |     |     |     | 45  |     |     |     |     | 50  |     |      |
| CTG | ACT | AAC | TGC | TTC | ATT | GTG | TCG | TTG | GCT | ATC | ACC | GAT | CTG | CTC | CTC | 368  |
| Leu | Thr | Asn | Cys | Phe | Ile | Val | Ser | Leu | Ala | Ile | Thr | Asp | Leu | Leu | Leu |      |
|     |     |     | 55  |     |     |     |     | 60  |     |     |     |     | 65  |     |     |      |
| GGC | CTC | CTG | GTG | CTG | CCC | TTC | TCG | GCC | TTC | TAC | CAG | CTA | TCC | TGC | AGG | 416  |
| Gly | Leu | Leu | Val | Leu | Pro | Phe | Ser | Ala | Phe | Tyr | Gln | Leu | Ser | Cys | Arg |      |
|     |     | 70  |     |     |     |     | 75  |     |     |     |     | 80  |     |     |     |      |
| TGG | AGC | TTC | GGC | AAA | GTC | TTC | TGC | AAT | ATC | TAT | ACC | AGC | TTG | GAT | GTG | 464  |
| Trp | Ser | Phe | Gly | Lys | Val | Phe | Cys | Asn | Ile | Tyr | Thr | Ser | Leu | Asp | Val |      |
|     | 85  |     |     |     |     | 90  |     |     |     |     | 95  |     |     |     |     |      |
| ATG | CTG | TGC | ACG | GCC | TCC | ATC | CTC | AAC | CTC | TTC | ATG | ATC | AGC | CTT | GAC | 512  |
| Met | Leu | Cys | Thr | Ala | Ser | Ile | Leu | Asn | Leu | Phe | Met | Ile | Ser | Leu | Asp |      |
| 100 |     |     |     |     | 105 |     |     |     |     | 110 |     |     |     |     | 115 |      |
| CGG | TAC | TGC | GCT | GTC | ACT | GAC | CCC | CTG | CGC | TAC | CCT | GTG | CTT | ATC | ACC | 560  |
| Arg | Tyr | Cys | Ala | Val | Thr | Asp | Pro | Leu | Arg | Tyr | Pro | Val | Leu | Ile | Thr |      |
|     |     |     |     | 120 |     |     |     |     | 125 |     |     |     |     | 130 |     |      |
| CCA | GTC | CGG | GTC | GCC | GTC | TCT | CTT | GTC | TTA | ATT | TGG | GTC | ATC | TCC | ATC | 608  |
| Pro | Val | Arg | Val | Ala | Val | Ser | Leu | Val | Leu | Ile | Trp | Val | Ile | Ser | Ile |      |
|     |     | 135 |     |     |     |     | 140 |     |     |     |     | 145 |     |     |     |      |
| ACC | CTG | TCC | TTC | CTG | TCT | ATT | CAT | CTG | GGG | TGG | AAC | AGC | AGG | AAT | GAG | 656  |
| Thr | Leu | Ser | Phe | Leu | Ser | Ile | His | Leu | Gly | Trp | Asn | Ser | Arg | Asn | Glu |      |
|     |     | 150 |     |     |     |     | 155 |     |     |     |     | 160 |     |     |     |      |
| ACC | AGC | AGT | TTC | AAT | CAC | ACC | ATT | CCC | AAG | TGC | AAA | GTC | CAG | GTC | AAC | 704  |
| Thr | Ser | Ser | Phe | Asn | His | Thr | Ile | Pro | Lys | Cys | Lys | Val | Gln | Val | Asn |      |
|     | 165 |     |     |     |     | 170 |     |     |     |     | 175 |     |     |     |     |      |
| TTG | GTG | TAT | GGC | TTG | GTG | GAT | GGG | CTG | GTC | ACC | TTC | TAC | CTG | CCG | CTG | 752  |
| Leu | Val | Tyr | Gly | Leu | Val | Asp | Gly | Leu | Val | Thr | Phe | Tyr | Leu | Pro | Leu |      |
| 180 |     |     |     |     | 185 |     |     |     |     | 190 |     |     |     |     | 195 |      |
| CTG | GTC | ATG | TGC | ATC | ACC | TAC | TAC | CGC | ATC | TTC | AAG | ATT | GCC | CGG | AGG | 800  |
| Leu | Val | Met | Cys | Ile | Thr | Tyr | Tyr | Arg | Ile | Phe | Lys | Ile | Ala | Arg | Arg |      |
|     |     |     |     | 200 |     |     |     |     | 205 |     |     |     |     | 210 |     |      |
| ATC | CAT | GAC | CAG | GCC | AAG | CAC | ATG | GGC | TCC | TGG | AAG | GCA | GCT | ACC | ATT | 848  |
| Ile | His | Asp | Gln | Ala | Lys | His | Met | Gly | Ser | Trp | Lys | Ala | Ala | Thr | Ile |      |
|     |     |     | 215 |     |     |     |     | 220 |     |     |     |     | 225 |     |     |      |
| GGG | GAG | CAC | AAA | GCC | ACA | GTG | ACA | CTG | GCT | GCA | GTG | ATG | GGA | GCC | TTC | 896  |
| Gly | Glu | His | Lys | Ala | Thr | Val | Thr | Leu | Ala | Ala | Val | Met | Gly | Ala | Phe |      |
|     |     | 230 |     |     |     |     | 235 |     |     |     |     | 240 |     |     |     |      |
| ATC | ATA | TGC | TGG | TTC | CCC | TAC | TTT | ACT | GTG | TTT | GTT | TAC | CGT | GGG | CTG | 944  |
| Ile | Ile | Cys | Trp | Phe | Pro | Tyr | Phe | Thr | Val | Phe | Val | Tyr | Arg | Gly | Leu |      |
|     | 245 |     |     |     |     | 250 |     |     |     |     | 255 |     |     |     |     |      |
| AAA | GGG | GAT | GAT | GCC | ATC | AAT | GAG | GCT | TTT | GAA | GCC | GTC | GTT | CTG | TGG | 992  |
| Lys | Gly | Asp | Asp | Ala | Ile | Asn | Glu | Ala | Phe | Glu | Ala | Val | Val | Leu | Trp |      |
| 260 |     |     |     |     | 265 |     |     |     |     | 270 |     |     |     |     | 275 |      |
| CTG | GGC | TAT | GCC | AAC | TCG | GCC | CTG | AAC | CCT | ATC | CTG | TAT | GCC | ACA | CTG | 1040 |
| Leu | Gly | Tyr | Ala | Asn | Ser | Ala | Leu | Asn | Pro | Ile | Leu | Tyr | Ala | Thr | Leu |      |
|     |     |     |     | 280 |     |     |     |     | 285 |     |     |     |     | 290 |     |      |
| AAC | AGA | GAC | TTC | CGC | ACG | GCA | TAC | CAA | CAG | CTC | TTC | CGC | TGC | AGG | CCG | 1088 |
| Asn | Arg | Asp | Phe | Arg | Thr | Ala | Tyr | Gln | Gln | Leu | Phe | Arg | Cys | Arg | Pro |      |
|     |     |     | 295 |     |     |     |     | 300 |     |     |     |     | 305 |     |     |      |
| GCC | AGC | CAC | AAT | GCC | CAG | GAA | ACT | TCT | CTG | AGG | TCG | AAC | AGC | TCT | CAG | 1136 |
| Ala | Ser | His | Asn | Ala | Gln | Glu | Thr | Ser | Leu | Arg | Ser | Asn | Ser | Ser | Gln |      |
|     |     | 310 |     |     |     |     | 315 |     |     |     |     | 320 |     |     |     |      |
| CTG | GCC | AGG | AAT | CAA | AGC | CGA | GAA | CCC | ATG | CGG | CAG | GAA | GAG | AAG | CCC | 1184 |
| Leu | Ala | Arg | Asn | Gln | Ser | Arg | Glu | Pro | Met | Arg | Gln | Glu | Glu | Lys | Pro |      |

```
                325                        330                           335
CTG  AAG  CTC  CAG  GTG  TGG  AGT  GGG  ACA  GAG  GTC  ACA  GCC  CCT  CGA  GGA       1232
Leu  Lys  Leu  Gln  Val  Trp  Ser  Gly  Thr  Glu  Val  Thr  Ala  Pro  Arg  Gly
340                      345                      350                      355

GCC  ACA  GAC  AGG  TAATTGCCCT  GACCATTTGT  GTACCAGACA  AGCGCCTGGG                    1284
Ala  Thr  Asp  Arg

GAGGGGGGT  GTCCCACTAG  TGACCACCAT  TAAGGGGATG  GCTGTTCCCC  AGGAGCTAGT                 1344

TGAACATTCT  GTGCTGGGAA  GTTTTCATGA  GCACTTTGCA  AACCTCATGT  TGTTCCATCC                1404

TCCCAATGGC  CTCCT                                                                    1419
```

( 2 ) INFORMATION FOR SEQ ID NO:6:

( i ) SEQUENCE CHARACTERISTICS:
        ( A ) LENGTH: 359 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Met  Ile  Ser  Asn  Gly  Thr  Gly  Ser  Ser  Phe  Cys  Leu  Asp  Ser  Pro  Pro
 1                  5                        10                       15

Cys  Arg  Ile  Thr  Val  Ser  Val  Val  Leu  Thr  Val  Leu  Ile  Leu  Ile  Thr
               20                       25                       30

Ile  Ala  Gly  Asn  Val  Val  Val  Cys  Leu  Ala  Val  Gly  Leu  Asn  Arg  Arg
               35                       40                       45

Leu  Arg  Ser  Leu  Thr  Asn  Cys  Phe  Ile  Val  Ser  Leu  Ala  Ile  Thr  Asp
          50                       55                       60

Leu  Leu  Leu  Gly  Leu  Leu  Val  Leu  Pro  Phe  Ser  Ala  Phe  Tyr  Gln  Leu
65                       70                       75                            80

Ser  Cys  Arg  Trp  Ser  Phe  Gly  Lys  Val  Phe  Cys  Asn  Ile  Tyr  Thr  Ser
                    85                       90                       95

Leu  Asp  Val  Met  Leu  Cys  Thr  Ala  Ser  Ile  Leu  Asn  Leu  Phe  Met  Ile
                    100                      105                      110

Ser  Leu  Asp  Arg  Tyr  Cys  Ala  Val  Thr  Asp  Pro  Leu  Arg  Tyr  Pro  Val
               115                      120                      125

Leu  Ile  Thr  Pro  Val  Arg  Val  Ala  Val  Ser  Leu  Val  Leu  Ile  Trp  Val
          130                      135                      140

Ile  Ser  Ile  Thr  Leu  Ser  Phe  Leu  Ser  Ile  His  Leu  Gly  Trp  Asn  Ser
145                      150                      155                           160

Arg  Asn  Glu  Thr  Ser  Ser  Phe  Asn  His  Thr  Ile  Pro  Lys  Cys  Lys  Val
                    165                      170                      175

Gln  Val  Asn  Leu  Val  Tyr  Gly  Leu  Val  Asp  Gly  Leu  Val  Thr  Phe  Tyr
               180                      185                      190

Leu  Pro  Leu  Leu  Val  Met  Cys  Ile  Thr  Tyr  Tyr  Arg  Ile  Phe  Lys  Ile
          195                      200                      205

Ala  Arg  Arg  Ile  His  Asp  Gln  Ala  Lys  His  Met  Gly  Ser  Trp  Lys  Ala
     210                      215                      220

Ala  Thr  Ile  Gly  Glu  His  Lys  Ala  Thr  Val  Thr  Leu  Ala  Ala  Val  Met
225                      230                      235                           240

Gly  Ala  Phe  Ile  Ile  Cys  Trp  Phe  Pro  Tyr  Phe  Thr  Val  Phe  Val  Tyr
               245                      250                      255

Arg  Gly  Leu  Lys  Gly  Asp  Asp  Ala  Ile  Asn  Glu  Ala  Phe  Glu  Ala  Val
               260                      265                      270

Val  Leu  Trp  Leu  Gly  Tyr  Ala  Asn  Ser  Ala  Leu  Asn  Pro  Ile  Leu  Tyr
          275                      280                      285
```

Ala Thr Leu Asn Arg Asp Phe Arg Thr Ala Tyr Gln Gln Leu Phe Arg
290                     295                     300

Cys Arg Pro Ala Ser His Asn Ala Gln Glu Thr Ser Leu Arg Ser Asn
305                     310                     315                     320

Ser Ser Gln Leu Ala Arg Asn Gln Ser Arg Glu Pro Met Arg Gln Glu
            325                     330                     335

Glu Lys Pro Leu Lys Leu Gln Val Trp Ser Gly Thr Glu Val Thr Ala
            340                     345                     350

Pro Arg Gly Ala Thr Asp Arg
            355

(2) INFORMATION FOR SEQ ID NO:7:

(i) SEQUENCE CHARACTERISTICS:
    (A) LENGTH: 359 amino acids
    (B) TYPE: amino acid
    (D) TOPOLOGY: unknown (ii) MOLECULE TYPE: protein (vi) ORIGINAL SOURCE:
    (A) ORGANISM: Dog (xi) SEQUENCE DESCRIPTION: SEQ ID NO:7:

Met Ile Ser Asn Gly Thr Gly Ser Ser Phe Cys Leu Asp Ser Pro Pro
1               5                       10                      15

Cys Arg Ile Thr Val Ser Val Val Leu Thr Val Leu Ile Leu Ile Thr
            20                      25                      30

Ile Ala Gly Asn Val Val Val Cys Leu Ala Val Gly Leu Asn Arg Arg
            35                      40                      45

Leu Arg Ser Leu Thr Asn Cys Phe Ile Val Ser Leu Ala Ile Thr Asp
    50                      55                      60

Leu Leu Leu Gly Leu Leu Val Leu Pro Phe Ser Ala Phe Tyr Gln Leu
65                      70                      75                      80

Ser Cys Arg Trp Ser Phe Gly Lys Val Phe Cys Asn Ile Tyr Thr Ser
                85                      90                      95

Leu Asp Val Met Leu Cys Thr Ala Ser Ile Leu Asn Leu Phe Met Ile
            100                     105                     110

Ser Leu Asp Arg Tyr Cys Ala Val Thr Asp Pro Leu Arg Tyr Pro Val
            115                     120                     125

Leu Ile Thr Pro Val Arg Val Ala Val Ser Leu Val Leu Ile Trp Val
            130                     135                     140

Ile Ser Ile Thr Leu Ser Phe Leu Ser Ile His Leu Gly Trp Asn Ser
145                     150                     155                     160

Thr Asn Glu Thr Ser Ser Phe Asn His Thr Ile Pro Lys Cys Lys Val
                165                     170                     175

Gln Val Asn Leu Val Tyr Gly Leu Val Asp Gly Leu Val Thr Phe Tyr
            180                     185                     190

Leu Pro Leu Leu Val Met Cys Ile Thr Tyr Tyr Arg Ile Phe Lys Ile
            195                     200                     205

Ala Arg Asp Gln Ala Lys Arg Ile His His Met Gly Ser Trp Lys Ala
            210                     215                     220

Ala Thr Ile Gly Glu His Lys Ala Thr Val Thr Leu Ala Ala Val Met
225                     230                     235                     240

Gly Ala Phe Ile Ile Cys Trp Phe Pro Tyr Phe Thr Val Phe Val Tyr
                245                     250                     255

Arg Gly Leu Lys Gly Asp Asp Ala Ile Asn Glu Ala Phe Glu Ala Val

|     |     |     |     |     | 260 |     |     |     |     | 265 |     |     |     |     | 270 |     |     |
| --- | --- | --- | --- | --- | --- | --- | --- | --- | --- | --- | --- | --- | --- | --- | --- | --- | --- |
| Val | Leu | Trp | Leu | Gly | Tyr | Ala | Asn | Ser | Ala | Leu | Asn | Pro | Ile | Leu | Tyr |
|     |     | 275 |     |     |     |     | 280 |     |     |     |     | 285 |     |     |     |
| Ala | Thr | Leu | Asn | Arg | Asp | Phe | Arg | Thr | Ala | Tyr | Gln | Gln | Leu | Phe | Arg |
|     |     | 290 |     |     |     |     | 295 |     |     |     |     | 300 |     |     |     |
| Cys | Arg | Pro | Ala | Ser | His | Asn | Ala | Gln | Glu | Thr | Ser | Leu | Arg | Ser | Asn |
| 305 |     |     |     |     | 310 |     |     |     |     | 315 |     |     |     |     | 320 |
| Ser | Ser | Gln | Leu | Ala | Arg | Asn | Gln | Ser | Arg | Glu | Pro | Met | Arg | Gln | Glu |
|     |     |     |     | 325 |     |     |     |     | 330 |     |     |     |     | 335 |     |
| Glu | Lys | Pro | Leu | Lys | Leu | Gln | Val | Trp | Ser | Gly | Thr | Glu | Val | Thr | Ala |
|     |     |     | 340 |     |     |     |     | 345 |     |     |     |     | 350 |     |     |
| Pro | Arg | Gly | Ala | Thr | Asp | Arg |
|     |     | 355 |     |     |     |     |

( 2 ) INFORMATION FOR SEQ ID NO:8:

( i ) SEQUENCE CHARACTERISTICS:
        ( A ) LENGTH: 419 amino acids
        ( B ) TYPE: amino acid
        ( D ) TOPOLOGY: unknown ( i i ) MOLECULE TYPE: protein ( v i ) ORIGINAL SOURCE:
        ( A ) ORGANISM: Hamster ( x i ) SEQUENCE DESCRIPTION: SEQ ID NO:8:

| Met | Gly | Pro | Pro | Gly | Asn | Asp | Ser | Asp | Phe | Leu | Leu | Thr | Thr | Asn | Gly |
| --- | --- | --- | --- | --- | --- | --- | --- | --- | --- | --- | --- | --- | --- | --- | --- |
| 1   |     |     |     | 5   |     |     |     |     | 10  |     |     |     |     | 15  |     |
| Ser | His | Val | Pro | Asp | His | Asp | Val | Thr | Glu | Glu | Arg | Asp | Glu | Ala | Trp |
|     |     |     | 20  |     |     |     |     | 25  |     |     |     |     | 30  |     |     |
| Val | Val | Gly | Ala | Ile | Leu | Met | Ser | Val | Ile | Val | Leu | Ala | Ile | Val | Gly |
|     |     |     | 35  |     |     |     |     | 40  |     |     |     |     | 45  |     |     |
| Gly | Phe | Gly | Asn | Val | Leu | Val | Ile | Thr | Ala | Ile | Ala | Lys | Phe | Glu | Arg |
|     |     | 50  |     |     |     |     | 55  |     |     |     |     | 60  |     |     |     |
| Leu | Gln | Thr | Val | Thr | Asn | Tyr | Phe | Ile | Thr | Ser | Leu | Ala | Cys | Ala | Asp |
| 65  |     |     |     |     | 70  |     |     |     |     | 75  |     |     |     |     | 80  |
| Leu | Val | Met | Gly | Leu | Ala | Val | Val | Pro | Phe | Gly | Ala | Ser | His | Ile | Leu |
|     |     |     |     | 85  |     |     |     |     | 90  |     |     |     |     | 95  |     |
| Met | Lys | Met | Trp | Asn | Phe | Gly | Asn | Phe | Trp | Cys | Glu | Phe | Trp | Thr | Ser |
|     |     |     | 100 |     |     |     |     | 105 |     |     |     |     | 110 |     |     |
| Ile | Asp | Val | Leu | Cys | Val | Thr | Ala | Ser | Ile | Glu | Thr | Leu | Cys | Val | Ile |
|     |     |     | 115 |     |     |     |     | 120 |     |     |     |     | 125 |     |     |
| Ala | Val | Asp | Arg | Tyr | Ile | Ala | Ile | Thr | Ser | Pro | Phe | Lys | Tyr | Gln | Ser |
|     |     | 130 |     |     |     |     | 135 |     |     |     |     | 140 |     |     |     |
| Leu | Leu | Thr | Lys | Asn | Lys | Ala | Arg | Met | Val | Ile | Leu | Met | Val | Trp | Ile |
| 145 |     |     |     |     | 150 |     |     |     |     | 155 |     |     |     |     | 160 |
| Val | Ser | Gly | Leu | Thr | Ser | Phe | Leu | Pro | Ile | Gln | Met | His | Trp | Tyr | Arg |
|     |     |     |     | 165 |     |     |     |     | 170 |     |     |     |     | 175 |     |
| Ala | Thr | His | Gln | Lys | Ala | Ile | Asp | Cys | Tyr | His | Lys | Glu | Thr | Cys | Cys |
|     |     |     | 180 |     |     |     |     | 185 |     |     |     |     | 190 |     |     |
| Asp | Phe | Phe | Thr | Met | Gln | Ala | Tyr | Ala | Ile | Ala | Ser | Ser | Ile | Val | Ser |
|     |     | 195 |     |     |     |     | 200 |     |     |     |     | 205 |     |     |     |
| Phe | Tyr | Val | Pro | Leu | Val | Val | Asn | Val | Phe | Val | Tyr | Ser | Arg | Val | Phe |
|     |     | 210 |     |     |     |     | 215 |     |     |     |     | 220 |     |     |     |
| Gln | Val | Glu | Gly | Arg | Phe | His | Ser | Pro | Asn | Leu | Ala | Lys | Arg | Gln | Leu |
| 225 |     |     |     |     | 230 |     |     |     |     | 235 |     |     |     |     | 240 |

| | | | | | | | | | | | | | | |
|---|---|---|---|---|---|---|---|---|---|---|---|---|---|---|
|Gln|Lys|Ile|Asp|Ile|Ser|Gly|Gln|Val|Glu|Gln|Asp|Gly|Arg|Ser|Gly|
| | | | |245| | | |250| | | | |255| | |
|His|Gly|Leu|Arg|Arg|Ser|Ser|Lys|Phe|Cys|Leu|Lys|Glu|His|Lys|Ala|
| | | | |260| | | |265| | | | |270| | |
|Leu|Lys|Thr|Leu|Gly|Ile|Ile|Met|Gly|Thr|Phe|Thr|Leu|Cys|Trp|Leu|
| | | |275| | | |280| | | | |285| | | |
|Pro|Phe|Phe|Ile|Val|Asn|Ile|Val|His|Val|Ile|Gln|Asp|Asn|Leu|Ile|
| | |290| | | |295| | | | |300| | | | |
|Pro|Lys|Glu|Val|Tyr|Ile|Leu|Leu|Asn|Trp|Leu|Gly|Tyr|Val|Asn|Ser|
|305| | | | |310| | | |315| | | | | |320|
|Ala|Phe|Asn|Pro|Leu|Ile|Tyr|Cys|Arg|Ser|Pro|Asp|Phe|Arg|Ile|Ala|
| | | | |325| | | |330| | | | |335| | |
|Phe|Gln|Glu|Leu|Leu|Cys|Leu|Arg|Arg|Ser|Ser|Ser|Lys|Ala|Tyr|Gly|
| | | |340| | | |345| | | | |350| | | |
|Asn|Gly|Tyr|Ser|Ser|Asn|Ser|Asn|Gly|Lys|Thr|Asp|Tyr|Met|Gly|Glu|
| | |355| | | |360| | | | |365| | | | |
|Ala|Ser|Gly|Cys|Gln|Leu|Gly|Gln|Glu|Lys|Glu|Ser|Glu|Arg|Leu|Cys|
| |370| | | |375| | | | |380| | | | | |
|Glu|Asp|Pro|Pro|Gly|Thr|Glu|Ser|Phe|Val|Asn|Cys|Gln|Gly|Thr|Val|
|385| | | |390| | | | |395| | | | | |400|
|Pro|Ser|Leu|Ser|Leu|Asp|Ser|Gln|Gly|Arg|Asn|Cys|Ser|Thr|Asn|Asp|
| | | |405| | | | |410| | | |415| | | |
|Ser|Pro|Leu| | | | | | | | | | | | | |

( 2 ) INFORMATION FOR SEQ ID NO:9:

( i ) SEQUENCE CHARACTERISTICS:
        ( A ) LENGTH: 400 amino acids
        ( B ) TYPE: amino acid
        ( D ) TOPOLOGY: unknown ( i i ) MOLECULE TYPE: protein ( v i ) ORIGINAL SOURCE:
        ( A ) ORGANISM: Homo sapiens ( x i ) SEQUENCE DESCRIPTION: SEQ ID NO:9:

| | | | | | | | | | | | | | | |
|---|---|---|---|---|---|---|---|---|---|---|---|---|---|---|
|Met|Ala|Pro|Trp|Pro|His|Glu|Asn|Ser|Ser|Leu|Ala|Pro|Trp|Pro|Asp|
|1| | | |5| | | |10| | | |15| | | |
|Leu|Pro|Thr|Leu|Ala|Pro|Asn|Thr|Ala|Asn|Thr|Ser|Gly|Leu|Pro|Gly|
| | | |20| | | |25| | | | |30| | | |
|Val|Pro|Trp|Glu|Ala|Ala|Leu|Ala|Gly|Ala|Leu|Leu|Ala|Leu|Ala|Val|
| | | |35| | | |40| | | | |45| | | |
|Leu|Ala|Thr|Val|Asn|Leu|Leu|Val|Ile|Val|Ala|Ile|Ala|Trp|Thr|Pro|
| |50| | | | |55| | | | |60| | | | |
|Arg|Leu|Gln|Thr|Asn|Thr|Asn|Val|Phe|Val|Thr|Ser|Leu|Ala|Ala|Ala|
|65| | | | |70| | | |75| | | | | |80|
|Asp|Leu|Val|Met|Gly|Leu|Leu|Val|Val|Pro|Pro|Ala|Ala|Thr|Leu|Ala|
| | | | |85| | | |90| | | | |95| | |
|Leu|Thr|Gly|His|Trp|Pro|Leu|Gly|Ala|Thr|Gly|Cys|Glu|Leu|Trp|Thr|
| | | |100| | | |105| | | | |110| | | |
|Ser|Val|Asp|Val|Leu|Cys|Val|Thr|Ala|Ser|Ile|Glu|Thr|Leu|Cys|Ala|
| | |115| | | |120| | | | |125| | | | |
|Leu|Ala|Val|Asp|Arg|Tyr|Leu|Ala|Val|Thr|Asn|Thr|Leu|Arg|Tyr|Gly|
| |130| | | | |135| | | | |140| | | | |
|Ala|Leu|Val|Thr|Lys|Arg|Cys|Ala|Arg|Thr|Ala|Val|Val|Leu|Val|Trp|
|145| | | | |150| | | |155| | | | | |160|

| | | | | | | | | | | | | | | |
|---|---|---|---|---|---|---|---|---|---|---|---|---|---|---|
|Val|Val|Ser|Ala|Ala 165|Val|Ser|Phe|Ala|Pro 170|Ile|Met|Ser|Gln|Trp Trp 175|
|Arg|Val|Gly|Ala 180|Asp|Ala|Glu|Ala|Gln 185|Arg|Cys|His|Ser|Asn 190|Pro Arg|
|Cys|Cys|Ala 195|Phe|Ala|Ser|Asn|Met 200|Pro|Tyr|Val|Leu|Leu 205|Ser|Ser Ser|
|Val|Ser 210|Phe|Tyr|Leu|Pro|Leu 215|Leu|Val|Met|Leu|Phe 220|Val|Tyr|Ala Arg|
|Val 225|Phe|Val|Val|Ala|Thr 230|Arg|Gln|Leu|Arg|Leu 235|Leu|Arg|Gly|Glu Leu 240|
|Gly|Arg|Phe|Pro|Pro 245|Glu|Glu|Ser|Pro|Ala 250|Pro|Pro|Ser|Arg|Ser Leu 255|
|Ala|Pro|Ala|Pro 260|Val|Gly|Thr|Cys|Ala 265|Pro|Pro|Glu|Gly|Val 270|Pro Ala|
|Cys|Gly|Arg 275|Arg|Pro|Ala|Arg|Leu 280|Leu|Pro|Leu|Arg|Glu 285|His|Arg Ala|
|Leu|Cys 290|Thr|Leu|Gly|Leu|Ile 295|Met|Gly|Thr|Phe|Thr 300|Leu|Cys|Trp Leu|
|Pro 305|Phe|Phe|Leu|Ala|Asn 310|Val|Leu|Arg|Ala|Leu 315|Gly|Gly|Pro|Ser Leu 320|
|Val|Pro|Gly|Pro|Ala 325|Phe|Leu|Ala|Leu|Asn 330|Trp|Leu|Gly|Tyr|Ala Asn 335|
|Ser|Ala|Phe|Asn 340|Pro|Leu|Ile|Tyr|Cys 345|Arg|Ser|Pro|Asp|Phe 350|Arg Ser|
|Ala|Phe|Arg 355|Arg|Leu|Leu|Cys|Arg 360|Cys|Gly|Arg|Arg|Leu 365|Pro|Pro Glu|
|Pro|Cys 370|Ala|Ala|Ala|Arg|Pro 375|Ala|Leu|Phe|Pro|Ser 380|Gly|Val|Pro Ala|
|Ala 385|Arg|Ser|Ser|Pro|Ala 390|Gln|Pro|Arg|Leu|Cys 395|Gln|Arg|Leu|Asp Gly 400|

(2) INFORMATION FOR SEQ ID NO:10:

(i) SEQUENCE CHARACTERISTICS:
        (A) LENGTH: 384 amino acids
        (B) TYPE: amino acid
        (D) TOPOLOGY: unknown (ii) MOLECULE TYPE: protein (vi) ORIGINAL SOURCE:
        (A) ORGANISM: Bos taurus (xi) SEQUENCE DESCRIPTION: SEQ ID NO:10:

| | | | | | | | | | | | | | | |
|---|---|---|---|---|---|---|---|---|---|---|---|---|---|---|
|Met 1|Gly|Ala|Cys|Val 5|Val|Met|Thr|Asp|Ile 10|Asn|Ile|Ser|Ser|Gly Leu 15|
|Asp|Ser|Asn|Ala 20|Thr|Gly|Ile|Thr|Ala 25|Phe|Ser|Met|Pro|Gly 30|Trp Gln|
|Leu|Ala|Leu 35|Trp|Thr|Ala|Ala|Tyr 40|Leu|Ala|Leu|Val|Leu 45|Val|Ala Val|
|Met|Gly 50|Asn|Ala|Thr|Val|Ile 55|Trp|Ile|Ile|Leu|Ala 60|His|Gln|Arg Met|
|Arg 65|Thr|Val|Thr|Asn|Tyr 70|Phe|Ile|Val|Asn|Leu 75|Ala|Leu|Ala|Asp Leu 80|
|Cys|Met|Ala|Ala|Phe 85|Asn|Ala|Ala|Phe|Asn 90|Phe|Val|Tyr|Ala|Ser His 95|
|Asn|Ile|Trp|Tyr|Phe 100|Gly|Arg|Ala|Phe 105|Cys|Tyr|Phe|Gln|Asn 110|Leu Phe|

|     |     |     |     |     |     |     |     |     |     |     |     |     |     |     |
|-----|-----|-----|-----|-----|-----|-----|-----|-----|-----|-----|-----|-----|-----|-----|
| Pro | Ile | Thr | Ala | Met | Phe | Val | Ser | Ile | Tyr | Ser | Met | Thr | Ala | Ile | Ala |
|     | 115 |     |     |     |     | 120 |     |     |     |     | 125 |     |     |     |
| Ala | Asp | Arg | Tyr | Met | Ala | Ile | Val | His | Pro | Phe | Gln | Pro | Arg | Leu | Ser |
|     | 130 |     |     |     |     | 135 |     |     |     |     | 140 |     |     |     |
| Ala | Pro | Gly | Thr | Arg | Ala | Val | Ile | Ala | Gly | Ile | Trp | Leu | Val | Ala | Leu |
| 145 |     |     |     |     | 150 |     |     |     |     | 155 |     |     |     |     | 160 |
| Ala | Leu | Ala | Phe | Pro | Gln | Cys | Phe | Tyr | Ser | Thr | Ile | Thr | Thr | Asp | Glu |
|     |     |     |     | 165 |     |     |     |     | 170 |     |     |     |     | 175 |     |
| Gly | Ala | Thr | Lys | Cys | Val | Val | Ala | Trp | Pro | Glu | Asp | Ser | Gly | Gly | Lys |
|     |     |     | 180 |     |     |     |     | 185 |     |     |     |     | 190 |     |     |
| Met | Leu | Leu | Leu | Tyr | His | Leu | Ile | Val | Ile | Ala | Leu | Ile | Tyr | Phe | Leu |
|     |     | 195 |     |     |     |     | 200 |     |     |     |     | 205 |     |     |     |
| Pro | Leu | Val | Val | Met | Phe | Val | Ala | Tyr | Ser | Val | Ile | Gly | Leu | Thr | Leu |
|     | 210 |     |     |     |     | 215 |     |     |     |     | 220 |     |     |     |     |
| Trp | Arg | Arg | Ser | Val | Pro | Gly | His | Gln | Ala | His | Gly | Ala | Asn | Leu | Arg |
| 225 |     |     |     |     | 230 |     |     |     |     | 235 |     |     |     |     | 240 |
| His | Leu | Gln | Ala | Lys | Lys | Lys | Phe | Val | Lys | Thr | Met | Val | Leu | Val | Val |
|     |     |     |     | 245 |     |     |     |     | 250 |     |     |     |     | 255 |     |
| Val | Thr | Phe | Ala | Ile | Cys | Trp | Leu | Pro | Tyr | His | Leu | Tyr | Phe | Ile | Leu |
|     |     |     | 260 |     |     |     |     | 265 |     |     |     |     | 270 |     |     |
| Gly | Thr | Phe | Gln | Glu | Asp | Ile | Tyr | Cys | His | Lys | Phe | Ile | Gln | Gln | Val |
|     |     | 275 |     |     |     |     | 280 |     |     |     |     | 285 |     |     |     |
| Tyr | Leu | Ala | Leu | Phe | Trp | Leu | Ala | Met | Ser | Ser | Thr | Met | Tyr | Asn | Pro |
|     | 290 |     |     |     |     | 295 |     |     |     |     | 300 |     |     |     |     |
| Ile | Ile | Tyr | Cys | Cys | Leu | Asn | His | Arg | Phe | Arg | Ser | Gly | Phe | Arg | Leu |
| 305 |     |     |     |     | 310 |     |     |     |     | 315 |     |     |     |     | 320 |
| Ala | Phe | Arg | Cys | Cys | Pro | Trp | Val | Thr | Pro | Thr | Glu | Glu | Asp | Lys | Met |
|     |     |     |     | 325 |     |     |     |     | 330 |     |     |     |     | 335 |     |
| Glu | Leu | Thr | Tyr | Thr | Pro | Ser | Leu | Ser | Thr | Arg | Val | Asn | Arg | Cys | His |
|     |     |     | 340 |     |     |     |     | 345 |     |     |     |     | 350 |     |     |
| Thr | Lys | Glu | Ile | Phe | Phe | Met | Ser | Gly | Asp | Val | Ala | Pro | Ser | Glu | Ala |
|     |     | 355 |     |     |     |     | 360 |     |     |     |     | 365 |     |     |     |
| Val | Asn | Gly | Gln | Ala | Glu | Ser | Pro | Gln | Ala | Gly | Val | Ser | Thr | Glu | Pro |
|     |     | 370 |     |     |     |     | 375 |     |     |     |     | 380 |     |     |     |

( 2 ) INFORMATION FOR SEQ ID NO:11:

( i ) SEQUENCE CHARACTERISTICS:
        ( A ) LENGTH: 237 amino acids
        ( B ) TYPE: amino acid
        ( D ) TOPOLOGY: unknown ( i i ) MOLECULE TYPE: protein ( v ) FRAGMENT TYPE: N-terminal ( v i ) ORIGINAL SOURCE:
        ( A ) ORGANISM: Homo sapiens ( x i ) SEQUENCE DESCRIPTION: SEQ ID NO:11:

|     |     |     |     |     |     |     |     |     |     |     |     |     |     |     |     |
|-----|-----|-----|-----|-----|-----|-----|-----|-----|-----|-----|-----|-----|-----|-----|-----|
| Met | Phe | Val | Asn | Phe | Ile | Leu | Phe | Pro | Cys | Arg | Phe | Lys | Cys | Leu | Phe |
| 1   |     |     |     | 5   |     |     |     |     | 10  |     |     |     |     | 15  |     |
| Ala | Thr | Trp | Leu | Leu | Ile | Arg | Glu | Arg | Lys | Met | Asn | Asn | Ser | Thr | Asn |
|     |     |     | 20  |     |     |     |     | 25  |     |     |     |     | 30  |     |     |
| Ser | Ser | Asn | Asn | Ser | Leu | Ala | Leu | Thr | Ser | Pro | Tyr | Lys | Thr | Phe | Glu |
|     |     |     | 35  |     |     |     |     | 40  |     |     |     |     | 45  |     |     |
| Val | Val | Phe | Ile | Val | Leu | Val | Ala | Gly | Ser | Leu | Ser | Leu | Val | Thr | Ile |
|     | 50  |     |     |     |     | 55  |     |     |     |     | 60  |     |     |     |     |

| | | | | | | | | | | | | | | | |
|---|---|---|---|---|---|---|---|---|---|---|---|---|---|---|---|
| Ile | Gly | Asn | Ile | Leu | Val | Met | Val | Ser | Ile | Lys | Val | Asn | Arg | His | Leu |
| 65 | | | | 70 | | | | | 75 | | | | | | 80 |
| Gln | Thr | Val | Asn | Asn | Thr | Phe | Leu | Phe | Ser | Leu | Ala | Cys | Ala | Asp | Leu |
| | | | | 85 | | | | | 90 | | | | | 95 | |
| Ile | Ile | Gly | Val | Phe | Ser | Met | Asn | Leu | Tyr | Thr | Leu | Tyr | Thr | Val | Ile |
| | | | 100 | | | | | 105 | | | | | 110 | | |
| Gly | Tyr | Trp | Pro | Leu | Gly | Pro | Val | Val | Cys | Asp | Leu | Trp | Leu | Ala | Leu |
| | | | 115 | | | | 120 | | | | | 125 | | | |
| Asp | Tyr | Val | Val | Ser | Asn | Ala | Ser | Val | Met | Asn | Leu | Leu | Ile | Ile | Ser |
| | | 130 | | | | 135 | | | | | 140 | | | | |
| Phe | Asp | Arg | Tyr | Phe | Cys | Val | Thr | Lys | Pro | Leu | Thr | Tyr | Pro | Val | Lys |
| 145 | | | | | 150 | | | | | 155 | | | | | 160 |
| Arg | Thr | Thr | Lys | Met | Ala | Gly | Met | Met | Ile | Ala | Ala | Ala | Trp | Val | Leu |
| | | | | 165 | | | | | 170 | | | | | 175 | |
| Ser | Phe | Ile | Leu | Trp | Ala | Pro | Ala | Ile | Leu | Phe | Trp | Gln | Phe | Ile | Val |
| | | | 180 | | | | | 185 | | | | | 190 | | |
| Gly | Val | Arg | Thr | Val | Glu | Asp | Gly | Glu | Cys | Tyr | Ile | Gln | Phe | Phe | Ser |
| | | 195 | | | | | 200 | | | | | 205 | | | |
| Asn | Ala | Ala | Val | Thr | Phe | Gly | Thr | Ala | Ile | Ala | Ala | Phe | Tyr | Leu | Pro |
| | | 210 | | | | | 215 | | | | 220 | | | | |
| Val | Ile | Ile | Met | Thr | Val | Leu | Tyr | Trp | His | Ile | Ser | Val | | | |
| 225 | | | | | 230 | | | | | 235 | | | | | |

(2) INFORMATION FOR SEQ ID NO:12:

(i) SEQUENCE CHARACTERISTICS:
        (A) LENGTH: 105 amino acids
        (B) TYPE: amino acid
        (D) TOPOLOGY: unknown (ii) MOLECULE TYPE: protein (v) FRAGMENT TYPE: C-terminal (vi) ORIGINAL SOURCE:
        (A) ORGANISM: Homo sapiens (xi) SEQUENCE DESCRIPTION: SEQ ID NO:12:

| | | | | | | | | | | | | | | | |
|---|---|---|---|---|---|---|---|---|---|---|---|---|---|---|---|
| Ala | Arg | Lys | Ile | Val | Lys | Met | Thr | Lys | Gln | Pro | Ala | Lys | Lys | Lys | Pro |
| 1 | | | | 5 | | | | | 10 | | | | | 15 | |
| Pro | Pro | Ser | Arg | Glu | Lys | Lys | Val | Thr | Arg | Thr | Ile | Leu | Ala | Ile | Leu |
| | | | 20 | | | | | 25 | | | | | 30 | | |
| Leu | Ala | Phe | Ile | Ile | Thr | Trp | Ala | Pro | Tyr | Asn | Val | Met | Val | Leu | Ile |
| | | 35 | | | | | 40 | | | | | 45 | | | |
| Asn | Thr | Phe | Cys | Ala | Pro | Cys | Ile | Pro | Asn | Thr | Val | Trp | Thr | Ile | Gly |
| | 50 | | | | | 55 | | | | | 60 | | | | |
| Tyr | Trp | Leu | Cys | Tyr | Ile | Asn | Ser | Thr | Ile | Asn | Pro | Ala | Cys | Tyr | Ala |
| 65 | | | | | 70 | | | | | 75 | | | | | 80 |
| Leu | Cys | Asn | Ala | Thr | Phe | Lys | Lys | Thr | Phe | Lys | His | Leu | Leu | Met | Cys |
| | | | | 85 | | | | | 90 | | | | | 95 | |
| His | Tyr | Lys | Asn | Ile | Gly | Ala | Thr | Arg | | | | | | | |
| | | | 100 | | | | | 105 | | | | | | | |

(2) INFORMATION FOR SEQ ID NO:13:

(i) SEQUENCE CHARACTERISTICS:
        (A) LENGTH: 238 amino acids
        (B) TYPE: amino acid
        (D) TOPOLOGY: unknown (i i) MOLECULE TYPE: protein (v) FRAGMENT TYPE: N-terminal (v i) ORIGINAL SOURCE:
    (A) ORGANISM: rat (x i) SEQUENCE DESCRIPTION: SEQ ID NO:13:

| Met | Asp | Pro | Leu | Asn | Leu | Ser | Trp | Tyr | Asp | Asp | Leu | Glu | Arg | Gln |
|---|---|---|---|---|---|---|---|---|---|---|---|---|---|---|
| 1 | | | | 5 | | | | | 10 | | | | | 15 |
| Asn | Trp | Ser | Arg | Pro | Phe | Asn | Gly | Ser | Glu | Gly | Lys | Ala | Asp | Arg | Pro |
| | | | 20 | | | | 25 | | | | | 30 | | | |
| His | Tyr | Asn | Tyr | Tyr | Ala | Met | Leu | Leu | Thr | Leu | Leu | Ile | Phe | Ile | Ile |
| | | 35 | | | | 40 | | | | | 45 | | | | |
| Val | Phe | Gly | Asn | Val | Leu | Val | Cys | Met | Ala | Val | Ser | Arg | Glu | Lys | Ala |
| | 50 | | | | 55 | | | | | 60 | | | | | |
| Leu | Gln | Thr | Thr | Thr | Asn | Tyr | Leu | Ile | Val | Ser | Leu | Ala | Val | Ala | Asp |
| 65 | | | | | 70 | | | | | 75 | | | | | 80 |
| Leu | Leu | Val | Ala | Thr | Leu | Val | Met | Pro | Trp | Val | Val | Tyr | Leu | Glu | Val |
| | | | | 85 | | | | | 90 | | | | | 95 | |
| Val | Gly | Glu | Trp | Lys | Phe | Ser | Arg | Ile | His | Cys | Asp | Ile | Phe | Val | Thr |
| | | | 100 | | | | | 105 | | | | | 110 | | |
| Leu | Asp | Val | Met | Met | Cys | Thr | Ala | Ser | Ile | Leu | Asn | Leu | Cys | Ala | Ile |
| | | 115 | | | | | 120 | | | | | 125 | | | |
| Ser | Ile | Asp | Arg | Tyr | Thr | Ala | Val | Ala | Met | Pro | Met | Leu | Tyr | Asn | Thr |
| | 130 | | | | | 135 | | | | | 140 | | | | |
| Arg | Tyr | Ser | Ser | Lys | Arg | Arg | Val | Thr | Val | Met | Ile | Ala | Ile | Val | Trp |
| 145 | | | | | 150 | | | | | 155 | | | | | 160 |
| Val | Leu | Ser | Phe | Thr | Ile | Ser | Cys | Pro | Leu | Leu | Phe | Gly | Leu | Asn | Asn |
| | | | | 165 | | | | | 170 | | | | | 175 | |
| Thr | Asp | Gln | Asn | Glu | Cys | Ile | Ile | Ala | Asn | Pro | Ala | Phe | Val | Val | Tyr |
| | | | 180 | | | | | 185 | | | | | 190 | | |
| Ser | Ser | Ile | Val | Ser | Phe | Tyr | Val | Pro | Phe | Ile | Val | Thr | Leu | Leu | Val |
| | | 195 | | | | | 200 | | | | | 205 | | | |
| Tyr | Ile | Lys | Ile | Tyr | Ile | Val | Leu | Arg | Lys | Arg | Arg | Lys | Arg | Val | Asn |
| | 210 | | | | | 215 | | | | | 220 | | | | |
| Thr | Lys | Arg | Ser | Ser | Arg | Ala | Phe | Arg | Ala | Asn | Leu | Lys | Thr |
| 225 | | | | | 230 | | | | | 235 | | | |

(2) INFORMATION FOR SEQ ID NO:14:

(i) SEQUENCE CHARACTERISTICS:
        (A) LENGTH: 98 amino acids
        (B) TYPE: amino acid
        (D) TOPOLOGY: unknown (i i) MOLECULE TYPE: protein (v) FRAGMENT TYPE: C-terminal (v i) ORIGINAL SOURCE:
        (A) ORGANISM: rat (x i) SEQUENCE DESCRIPTION: SEQ ID NO:14:

| Phe | Phe | Glu | Ile | Gln | Thr | Met | Pro | Asn | Gly | Lys | Thr | Arg | Thr | Ser | Leu |
|---|---|---|---|---|---|---|---|---|---|---|---|---|---|---|---|
| 1 | | | | 5 | | | | | 10 | | | | | 15 | |
| Lys | Thr | Met | Ser | Arg | Arg | Lys | Leu | Ser | Gln | Gln | Lys | Glu | Lys | Lys | Ala |
| | | | 20 | | | | | 25 | | | | | 30 | | |
| Thr | Gln | Met | Leu | Ala | Ile | Val | Leu | Gly | Val | Phe | Ile | Ile | Cys | Trp | Leu |
| | | | | 35 | | | | | 40 | | | | | 45 | |

-continued

```
Pro  Phe  Phe  Ile  Thr  His  Ile  Leu  Asn  Ile  His  Cys  Asp  Cys  Asn  Ile
     50                  55                       60

His  Gln  Ser  Ser  Thr  Ala  Pro  Ser  His  Gly  Trp  Ala  Met  Ser  Thr  Val
65                       70                  75                            80

Pro  Ser  Thr  Pro  Ser  Thr  Pro  Pro  Ser  Thr  Ser  Ser  Ser  Ala  Arg
                    85                  90                            95

Pro  Ser
```

(2) INFORMATION FOR SEQ ID NO:15:

(i) SEQUENCE CHARACTERISTICS:
        (A) LENGTH: 27 amino acids
        (B) TYPE: amino acid
        (D) TOPOLOGY: linear (ii) MOLECULE TYPE: peptide (v) FRAGMENT TYPE: internal (vi) ORIGINAL SOURCE:
        (A) ORGANISM: Homo sapiens (xi) SEQUENCE DESCRIPTION: SEQ ID NO:15:

```
Cys  Asn  Ile  Tyr  Thr  Ser  Leu  Asp  Val  Met  Leu  Val  Thr  Ala  Ser  Ile
1                   5                        10                       15

Leu  Asn  Leu  Phe  Met  Met  Arg  Leu  Asp  Arg  Tyr
               20                  25
```

(2) INFORMATION FOR SEQ ID NO:16:

(i) SEQUENCE CHARACTERISTICS:
        (A) LENGTH: 27 amino acids
        (B) TYPE: amino acid
        (D) TOPOLOGY: linear (ii) MOLECULE TYPE: peptide (v) FRAGMENT TYPE: internal (vi) ORIGINAL SOURCE:
        (A) ORGANISM: dog (xi) SEQUENCE DESCRIPTION: SEQ ID NO:16:

```
Cys  Asn  Ile  Tyr  Thr  Ser  Leu  Asp  Val  Met  Leu  Cys  Thr  Ala  Ser  Ile
1                   5                        10                       15

Leu  Asn  Leu  Phe  Met  Ile  Ser  Leu  Asp  Arg  Tyr
               20                  25
```

(2) INFORMATION FOR SEQ ID NO:17:

(i) SEQUENCE CHARACTERISTICS:
        (A) LENGTH: 27 amino acids
        (B) TYPE: amino acid
        (D) TOPOLOGY: linear (ii) MOLECULE TYPE: peptide (v) FRAGMENT TYPE: internal (vi) ORIGINAL SOURCE:
        (A) ORGANISM: Homo sapiens (xi) SEQUENCE DESCRIPTION: SEQ ID NO:17:

```
Cys  Gly  Val  Tyr  Leu  Ala  Leu  Asp  Val  Leu  Phe  Cys  Thr  Ser  Ser  Ile
1                   5                        10                       15

Val  His  Leu  Cys  Ala  Ile  Ser  Leu  Asp  Arg  Tyr
               20                  25
```

( 2 ) INFORMATION FOR SEQ ID NO:18:

( i ) SEQUENCE CHARACTERISTICS:
        ( A ) LENGTH: 27 amino acids
        ( B ) TYPE: amino acid
        ( D ) TOPOLOGY: linear ( i i ) MOLECULE TYPE: peptide ( v ) FRAGMENT TYPE: internal ( v i ) ORIGINAL SOURCE:
        ( A ) ORGANISM: Homo sapiens ( x i ) SEQUENCE DESCRIPTION: SEQ ID NO:18:

```
Cys  Glu  Leu  Trp  Thr  Ser  Val  Asp  Val  Leu  Cys  Val  Thr  Ala  Ser  Ile
1                   5                        10                      15
Glu  Thr  Leu  Cys  Val  Ile  Ala  Leu  Asp  Arg  Tyr
               20                  25
```

( 2 ) INFORMATION FOR SEQ ID NO:19:

( i ) SEQUENCE CHARACTERISTICS:
        ( A ) LENGTH: 27 amino acids
        ( B ) TYPE: amino acid
        ( D ) TOPOLOGY: linear ( i i ) MOLECULE TYPE: peptide ( v ) FRAGMENT TYPE: internal ( v i ) ORIGINAL SOURCE:
        ( A ) ORGANISM: Hamster ( x i ) SEQUENCE DESCRIPTION: SEQ ID NO:19:

```
Cys  Glu  Phe  Trp  Thr  Ser  Ile  Asp  Val  Leu  Cys  Val  Thr  Ala  Ser  Ile
1                   5                        10                      15
Glu  Thr  Leu  Cys  Val  Ile  Ala  Val  Asp  Arg  Tyr
               20                  25
```

( 2 ) INFORMATION FOR SEQ ID NO:20:

( i ) SEQUENCE CHARACTERISTICS:
        ( A ) LENGTH: 27 amino acids
        ( B ) TYPE: amino acid
        ( D ) TOPOLOGY: linear ( i i ) MOLECULE TYPE: peptide ( v ) FRAGMENT TYPE: internal ( v i ) ORIGINAL SOURCE:
        ( A ) ORGANISM: Homo sapiens ( x i ) SEQUENCE DESCRIPTION: SEQ ID NO:20:

```
Cys  Glu  Leu  Trp  Thr  Ser  Val  Asp  Val  Leu  Cys  Val  Thr  Ala  Ser  Ile
1                   5                        10                      15
Glu  Thr  Leu  Cys  Ala  Leu  Ala  Val  Asp  Arg  Tyr
               20                  25
```

( 2 ) INFORMATION FOR SEQ ID NO:21:

( i ) SEQUENCE CHARACTERISTICS:
        ( A ) LENGTH: 27 amino acids
        ( B ) TYPE: amino acid
        ( D ) TOPOLOGY: linear ( i i ) MOLECULE TYPE: peptide ( v ) FRAGMENT TYPE: internal ( v i ) ORIGINAL SOURCE:
    ( A ) ORGANISM: Rat ( x i ) SEQUENCE DESCRIPTION: SEQ ID NO:21:

Cys Asp Ile Phe Val Thr Leu Asp Val Met Met Cys Thr Ala Ser Ile
1               5                   1 0                  1 5

Leu Asn Leu Cys Ala Ile Ser Ile Asp Arg Tyr
            2 0              2 5

( 2 ) INFORMATION FOR SEQ ID NO:22:

( i ) SEQUENCE CHARACTERISTICS:
       ( A ) LENGTH: 27 amino acids
       ( B ) TYPE: amino acid
       ( D ) TOPOLOGY: linear ( i i ) MOLECULE TYPE: peptide ( v ) FRAGMENT TYPE: internal ( v i ) ORIGINAL SOURCE:
       ( A ) ORGANISM: Homo sapiens ( x i ) SEQUENCE DESCRIPTION: SEQ ID NO:22:

Cys Asp Leu Trp Leu Ala Leu Asp Tyr Val Val Ser Asn Ala Ser Val
1               5                   1 0                  1 5

Met Asn Leu Leu Ile Ile Ser Phe Asp Arg Tyr
            2 0              2 5

( 2 ) INFORMATION FOR SEQ ID NO:23:

( i ) SEQUENCE CHARACTERISTICS:
       ( A ) LENGTH: 27 amino acids
       ( B ) TYPE: amino acid
       ( D ) TOPOLOGY: linear ( i i ) MOLECULE TYPE: peptide ( v ) FRAGMENT TYPE: internal ( v i ) ORIGINAL SOURCE:
       ( A ) ORGANISM: Rat ( x i ) SEQUENCE DESCRIPTION: SEQ ID NO:23:

Cys Lys Phe His Asn Phe Phe Pro Ile Ala Ala Leu Phe Ala Ser Ile
1               5                   1 0                  1 5

Tyr Ser Met Thr Ala Val Ala Phe Asp Arg Tyr
            2 0              2 5

( 2 ) INFORMATION FOR SEQ ID NO:24:

( i ) SEQUENCE CHARACTERISTICS:
       ( A ) LENGTH: 27 amino acids
       ( B ) TYPE: amino acid
       ( D ) TOPOLOGY: linear ( i i ) MOLECULE TYPE: peptide ( v ) FRAGMENT TYPE: internal ( v i ) ORIGINAL SOURCE:
       ( A ) ORGANISM: Bos taurus ( x i ) SEQUENCE DESCRIPTION: SEQ ID NO:24:

Cys Tyr Phe Gln Asn Leu Phe Pro Ile Thr Ala Met Phe Val Ser Ile
1               5                   1 0                  1 5

Tyr Ser Met Thr Ala Ile Ala Ala Asp Arg Tyr
            2 0              2 5

( 2 ) INFORMATION FOR SEQ ID NO:25:

( i ) SEQUENCE CHARACTERISTICS:
        ( A ) LENGTH: 28 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:25:

```
Tyr Thr Ile Val Thr Leu Ser Val Thr Phe Leu Phe Gly Tyr Asn Thr
1               5                   10                  15
Gly Leu Leu Leu Thr Ala Ile Ser Val Glu Arg Cys
            20                  25
```

( 2 ) INFORMATION FOR SEQ ID NO:26:

( i ) SEQUENCE CHARACTERISTICS:
        ( A ) LENGTH: 24 amino acids
        ( B ) TYPE: amino acid
        ( D ) TOPOLOGY: linear ( i i ) MOLECULE TYPE: peptide ( v ) FRAGMENT TYPE: internal ( v i ) ORIGINAL SOURCE:
        ( A ) ORGANISM: Homo sapiens ( x i ) SEQUENCE DESCRIPTION: SEQ ID NO:26:

```
Asn Glu Val Tyr Gly Leu Val Asp Gly Leu Val Thr Phe Tyr Leu Pro
1               5                   10                  15
Leu Leu Ile Met Cys Ile Thr Tyr
            20
```

( 2 ) INFORMATION FOR SEQ ID NO:27:

( i ) SEQUENCE CHARACTERISTICS:
        ( A ) LENGTH: 24 amino acids
        ( B ) TYPE: amino acid
        ( D ) TOPOLOGY: linear ( i i ) MOLECULE TYPE: peptide ( v ) FRAGMENT TYPE: internal ( v i ) ORIGINAL SOURCE:
        ( A ) ORGANISM: Dog ( x i ) SEQUENCE DESCRIPTION: SEQ ID NO:27:

```
Asn Leu Val Tyr Gly Leu Val Asp Gly Leu Val Thr Phe Tyr Leu Pro
1               5                   10                  15
Leu Leu Val Met Cys Ile Thr Tyr
            20
```

( 2 ) INFORMATION FOR SEQ ID NO:28:

( i ) SEQUENCE CHARACTERISTICS:
        ( A ) LENGTH: 24 amino acids
        ( B ) TYPE: amino acid
        ( D ) TOPOLOGY: linear ( i i ) MOLECULE TYPE: peptide ( v ) FRAGMENT TYPE: internal ( v i ) ORIGINAL SOURCE:

(A) ORGANISM: Homo sapiens (xi) SEQUENCE DESCRIPTION: SEQ ID NO:28:

Asn Arg Ala Tyr Ala Ile Ala Ser Ser Val Val Ser Phe Tyr Val Pro
1               5                   10                  15
Leu Cys Ile Met Ala Phe Val Tyr
                20

(2) INFORMATION FOR SEQ ID NO:29:

(i) SEQUENCE CHARACTERISTICS:
    (A) LENGTH: 24 amino acids
    (B) TYPE: amino acid
    (D) TOPOLOGY: linear (ii) MOLECULE TYPE: peptide (v) FRAGMENT TYPE: internal (vi) ORIGINAL SOURCE:
    (A) ORGANISM: Hamster (xi) SEQUENCE DESCRIPTION: SEQ ID NO:29:

Asn Gln Ala Tyr Ala Ile Ala Ser Ser Ile Val Ser Phe Tyr Val Pro
1               5                   10                  15
Leu Val Val Met Val Phe Val Tyr
                20

(2) INFORMATION FOR SEQ ID NO:30:

(i) SEQUENCE CHARACTERISTICS:
    (A) LENGTH: 24 amino acids
    (B) TYPE: amino acid
    (D) TOPOLOGY: linear (ii) MOLECULE TYPE: peptide (v) FRAGMENT TYPE: internal (vi) ORIGINAL SOURCE:
    (A) ORGANISM: Homo sapiens (xi) SEQUENCE DESCRIPTION: SEQ ID NO:30:

Asn Met Pro Tyr Val Leu Leu Ser Ser Val Ser Phe Tyr Leu Pro
1               5                   10                  15
Leu Leu Val Met Leu Phe Val Tyr
                20

(2) INFORMATION FOR SEQ ID NO:31:

(i) SEQUENCE CHARACTERISTICS:
    (A) LENGTH: 25 amino acids
    (B) TYPE: amino acid
    (D) TOPOLOGY: linear (ii) MOLECULE TYPE: peptide (v) FRAGMENT TYPE: internal (vi) ORIGINAL SOURCE:
    (A) ORGANISM: Hamster (xi) SEQUENCE DESCRIPTION: SEQ ID NO:31:

Glu Pro Phe Tyr Ala Leu Phe Ser Ser Leu Gly Ser Phe Tyr Ile Pro
1               5                   10                  15
Leu Ala Val Ile Leu Val Met Tyr Cys
                20              25

( 2 ) INFORMATION FOR SEQ ID NO:32:

( i ) SEQUENCE CHARACTERISTICS:
        ( A ) LENGTH: 28 amino acids
        ( B ) TYPE: amino acid
        ( D ) TOPOLOGY: linear ( i i ) MOLECULE TYPE: peptide ( v ) FRAGMENT TYPE: internal ( v i ) ORIGINAL SOURCE:
        ( A ) ORGANISM: Rat ( x i ) SEQUENCE DESCRIPTION: SEQ ID NO:32:

```
Asn Pro Ala Phe Val Val Tyr Ser Ser Ile Val Ser Phe Tyr Val Pro
1               5                   10                  15
Phe Ile Val Thr Leu Leu Val Tyr Ile Lys Ile Tyr
                20                  25
```

( 2 ) INFORMATION FOR SEQ ID NO:33:

( i ) SEQUENCE CHARACTERISTICS:
        ( A ) LENGTH: 23 amino acids
        ( B ) TYPE: amino acid
        ( D ) TOPOLOGY: linear ( i i ) MOLECULE TYPE: peptide ( v ) FRAGMENT TYPE: internal ( v i ) ORIGINAL SOURCE:
        ( A ) ORGANISM: Bos taurus ( x i ) SEQUENCE DESCRIPTION: SEQ ID NO:33:

```
Leu Leu Leu Tyr His Leu Ile Val Ile Ala Leu Ile Tyr Phe Leu Pro
1               5                   10                  15
Leu Val Val Met Phe Val Ala
                20
```

( 2 ) INFORMATION FOR SEQ ID NO:34:

( i ) SEQUENCE CHARACTERISTICS:
        ( A ) LENGTH: 22 amino acids
        ( B ) TYPE: amino acid
        ( D ) TOPOLOGY: linear ( i i ) MOLECULE TYPE: peptide ( v ) FRAGMENT TYPE: internal ( v i ) ORIGINAL SOURCE:
        ( A ) ORGANISM: Rat ( x i ) SEQUENCE DESCRIPTION: SEQ ID NO:34:

```
Glu Lys Ala Tyr His Ile Cys Val Thr Val Leu Ile Tyr Phe Leu Pro
1               5                   10                  15
Leu Leu Val Ile Gly Tyr
                20
```

( 2 ) INFORMATION FOR SEQ ID NO:35:

( i ) SEQUENCE CHARACTERISTICS:
        ( A ) LENGTH: 23 amino acids
        ( B ) TYPE: amino acid
        ( D ) TOPOLOGY: linear ( i i ) MOLECULE TYPE: peptide ( v ) FRAGMENT TYPE: internal ( v i ) ORIGINAL SOURCE:
    ( A ) ORGANISM: Homo sapiens ( x i ) SEQUENCE DESCRIPTION: SEQ ID NO:35:

```
Asn Ala Ala Val Thr Phe Gly Thr Ala Ile Ala Ala Phe Tyr Leu Pro
 1               5                  10                  15
Val Ile Ile Met Thr Val Leu
             20
```

( 2 ) INFORMATION FOR SEQ ID NO:36:

( i ) SEQUENCE CHARACTERISTICS:
        ( A ) LENGTH: 28 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:36:

```
Asp Cys Arg Ala Val Ile Ile Phe Ile Ala Ile Leu Ser Phe Leu Val
 1               5                  10                  15
Phe Thr Pro Leu Met Leu Val Ser Ser Thr Ile Leu
             20              25
```

( 2 ) INFORMATION FOR SEQ ID NO:37:

( i ) SEQUENCE CHARACTERISTICS:
        ( A ) LENGTH: 19 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:37:

```
Pro Ser Leu Ser Leu Asp Ser Gln Gly Arg Asn Cys Ser Thr Asn Asp
 1               5                  10                  15
Ser Pro Leu
```

( 2 ) INFORMATION FOR SEQ ID NO:38:

( i ) SEQUENCE CHARACTERISTICS:
        ( A ) LENGTH: 17 base pairs
        ( B ) TYPE: nucleic acid
        ( C ) STRANDEDNESS: unknown
        ( D ) TOPOLOGY: linear ( i i ) MOLECULE TYPE: DNA (genomic)

( x i ) SEQUENCE DESCRIPTION: SEQ ID NO:38:

CAGGATGATA TCTAACG                                    17

( 2 ) INFORMATION FOR SEQ ID NO:39:

( i ) SEQUENCE CHARACTERISTICS:
        ( A ) LENGTH: 18 base pairs
        ( B ) TYPE: nucleic acid
        ( C ) STRANDEDNESS: unknown
        ( D ) TOPOLOGY: linear ( i i ) MOLECULE TYPE: DNA (genomic)

( x i ) SEQUENCE DESCRIPTION: SEQ ID NO:39:

GTGTCGTTGG CTATCACC                                 18

( 2 ) INFORMATION FOR SEQ ID NO:40:

( i ) SEQUENCE CHARACTERISTICS:
  ( A ) LENGTH: 17 base pairs
  ( B ) TYPE: nucleic acid
  ( C ) STRANDEDNESS: unknown
  ( D ) TOPOLOGY: linear ( i i ) MOLECULE TYPE: DNA (genomic)

( x i ) SEQUENCE DESCRIPTION: SEQ ID NO:40:

TCCATTCTTA ACCTCTT                                                    17

( 2 ) INFORMATION FOR SEQ ID NO:41:

( i ) SEQUENCE CHARACTERISTICS:
    ( A ) LENGTH: 17 base pairs
    ( B ) TYPE: nucleic acid
    ( C ) STRANDEDNESS: unknown
    ( D ) TOPOLOGY: linear ( i i ) MOLECULE TYPE: DNA (genomic)

( x i ) SEQUENCE DESCRIPTION: SEQ ID NO:41:

AAGGTGACCA GCCCATC                                                    17

RECOMBINANT GENOMIC CLONE ENCODING THE HISTAMINE H2 RECEPTOR, METHODS FOR PRODUCTION THEREOF, AND PROTEIN PRODUCED THEREFROM

This application is a Continuation of application Ser. No. 07/633,060, filed on Dec. 24, 1990, now abandoned.

The subject matter enclosed in this document is the product of work supported by the National Institutes of Health (Grant No. R01 DK 34306).

BACKGROUND OF THE INVENTION

1. Field of the Invention

The invention relates to genomic clones encoding histamine receptors, recombinant histamine receptors, and methods for producing said genomic clones.

2. Discussion of the Background

Histamine is one of the major determinants of gastric acid secretion. Through its three known receptor subclasses (H1, H2 and H3), histamine has been shown to exert a broad array of physiological activity, including mediation of allergic and anaphylactic responses (H1), modulation of cardiac contractility and systemic blood pressure (H1 and H2), and mediation of neural function in the central nervous system (H3).

Perhaps the best known activity of histamine involves its relationship to gastric acid secretion (H2 only). Antagonism of the histamine ligand at the H2 receptor has been the cornerstone of a current $3 billion market for pharmacological treatment of acid-peptic disorders of the gastrointestinal tract. The need, and potential market for the histamine H2 receptor clone is enormous because this receptor is presumed to be the primary mediator of gastric acid secretion. However despite a wealth of pharmacological information, little else is known about the structure of the histamine receptors.

H1 receptors are the mediators of many allergic reactions such as are caused by hay fever and antihistamines are in widespread use for treatment of symptoms resulting from allergies. Currently there are few, if any, histamine H1 selective antagonists and it is thought that availability of a gene encoding this receptor will greatly facilitate the development of compounds useful for the treatment of common allergies.

The function of the histamine H3 receptor subclass is currently unknown, except that it is present in the brain and its function may be related to general neural activity and possible cognitive function. The availability of a recombinant clone encoding the histamine H3 receptor gene obtained with the use of the histamine H2 receptor gene as a probe would permit the discovery of the function of the H3 receptor more thoroughly and possibly lead to therapeutically useful neuroactive compounds.

Currently there is no structural information on any of the subclasses of the histamine receptor. It is known that each subclass of histamine receptor is concentrated in a different type of cell. Pharmacological behavior corresponding to the H1 subclass is readily displayed in, e.g., smooth muscle and capillary cells, whereas the H2 subclass is associated with stomach cells, notably gastric parietal cells, and the H3 subclass is associated with neural cells.

There is an ongoing search to develop better and more effective histamine antagonists. The availability of the histamine H2 receptor gene will facilitate the development of such compounds. Moreover, the gene encoding this receptor, once obtained, can be utilized to isolate the also much needed genes encoding the two other major subclasses of histamine receptors (H1 and H3).

SUMMARY OF THE INVENTION

Accordingly, one object of this invention is to provide DNA sequences encoding histamine H1, H2 and H3 receptors, cells transfected with these DNA sequences, and/ or proteins encoded by these DNA sequences and having the activity of histamine H1, H2 and H3 receptors.

It is another object of the invention to provide a method for obtaining histamine H1, H2 and H3 receptor clones, cells transfected with histamine H1, H2 and H3 receptor-encoding DNA sequences, and/or proteins having the activity of histamine H1, H2 and H3 receptors.

The present invention which satisfies all of the above objects of the invention and other objects, as can be seen from the description of the invention given hereinbelow, provides recombinant genomic clones encoding histamine H1, H2 and H3 receptors, a method for obtaining these, proteins encoded thereby and capable of selectively binding histamine, and cells transfected with the genomic clones capable of expressing the recombinant histamine-binding proteins.

BRIEF DESCRIPTION OF THE FIGURES

FIGS. 1 and 2 provide the nucleotide sequences of a human (SEQ ID NO:1) and of a canine histamine H2 receptor gene (SEQ ID NO:3), respectively. FIG. 1 further compares the human (SEQ ID NO:2) and canine (SEQ ID NO:4) sequences (SEQ ID NO:6). FIG. 2 provides the deduced amino acid sequence of the canine protein.

FIG. 3 provides a structural comparison of a recombinant histamine H2 receptor of the present invention with other G-protein linked receptors. The deduced amino acid sequences of the receptors (indicated by the conventional single letter abbreviations) are aligned on the basis of homologous regions which are underscored by the bold letters. The Roman numerals indicated the putative transmembrane domains. CANH2=canine H2 receptor (SEQ ID NO:7), HAMADB2=hamster beta 2 adrenergic receptor (SEQ ID NO:8), HUMADB3=human beta 3 adrenergic receptor (SEQ ID NO:9), BOVSUBK=bovine substance K receptor (SEQ ID NO:10), HUMACHRM2=human M2 muscarinic receptor (SEQ ID NOS:11–12), RATDOP 2=rat dopamine D2 receptor (SEQ ID NOS:13–14).

FIG. 4 provides structural comparisons of the third and fifth transmembrane regions of two of the histamine H2 receptors of the present invention (HUMH2=human H2 receptor; CANH2=canine H2 receptor) with those of other G-protein linked receptors (SEQ ID NOS:16–36). HUMADA2=human alpha 2 adrenergic receptor, HUMADB1=human beta 1 adrenergic receptor, RATSUBP=rat substance P receptor, MAS=mas oncogene. For other abbreviations please refer to the legend to FIG. 3.

DETAILED DESCRIPTION OF THE PREFERRED EMBODIMENTS

Figure 5:
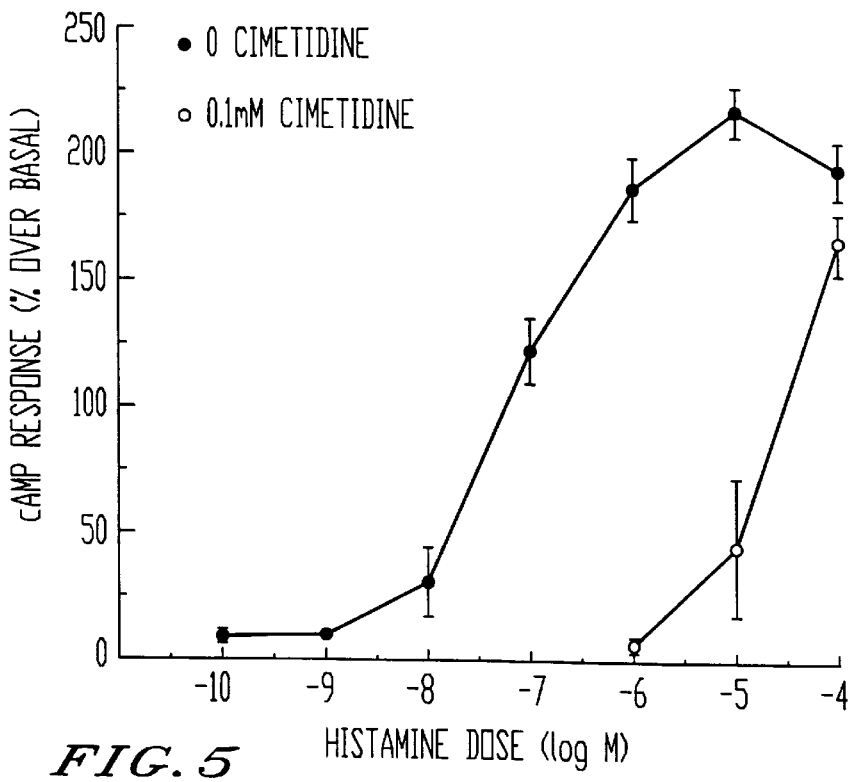
FIG. 5 is a graph displaying the dose-dependent response represented by production of cAMP to exogenously administered histamine in the absence or presence of cimetidine by L-cells transfected with a CMVneo vector containing the recombinant histamine H2 receptor gene insert.

In this text, the following standard nomenclature is used:

TABLE 1

Amino acid symbols

| Amino acid | Three-letter symbol | One-letter symbol |
| --- | --- | --- |
| Alanine | Ala | A |
| Arginine | Arg | R |
| Asparagine | Asn | N |
| Aspartic acid | Asp | D |
| Asn + Asp | Asx | B |
| Cysteine | Cys | C |
| Glutamine | Gln | Q |
| Glutamic acid | Glu | E |
| Gln + Glu | Glx | Z |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tryosine | Tyr | Y |
| Valine | Val | V |

The present discovery arose out of an effort by the inventors to study the mechanisms by which stimulants of gastric acid secretion act upon the parietal cell to generate hydrogen ions. Initial work by the inventors was focused around the purification and characterization of the receptor for gastrin, the major stimulant of acid secretion induced by eating a meal. However, in the process of attempting to isolate a recombinant clone encoding the gastrin receptor from a canine source, the inventors serendipitously cloned a histamine H2 receptor.

Because of the absence of any structural information on histamine H2 receptors, prior to the present invention, there was no indication as to how one might accomplish the cloning of a histamine H2 receptor gene. In the present invention, the inventors were fortunate of having been able to surmise the possibility that the clone they had isolated in their attempt to isolate a recombinant clone encoding for gastrin receptor, because of its specific characteristics, might represent a histamine receptor gene. Experiments (described infra) were performed by the inventors on the isolated clone to express the gene in heterologous cells. These experiments confirmed that the inventors had cloned the histamine H2 receptor gene.

The first histamine H2 receptor clone obtained by the inventors was isolated from a canine source. Since it is known that each subclass of histamine receptor, i.e., histamine H1, H2 and H3 receptors, is concentrated in a different type of cell, having obtained a histamine H2 receptor clone from a canine source, cDNA from this canine histamine H2 receptor clone was used to isolate a histamine H2 receptor clone from a human source. This human histamine H2 receptor clone can be used to isolate the genes encoding the other major subclasses of histamine receptors (H1 and H3).
1. Method for Obtaining the Histamine H1, H2 and H3 Genes:

On the gastric parietal cell, histamine exerts its stimulating action through an H2 subclass of receptor coupled via a guanine nucleotide binding protein (G-protein) to activation of adenylate cyclase and production of 3',5'-cyclic adenosine monophosphate (cAMP). In recent years, the genes for a family of G-protein linked receptors have been cloned. Analysis of the deduced structures of their proteins indicated that they have a seven transmembrane motif.

The amino acid sequences comprising the transmembrane regions are similar. A strategy based on use of synthetic oligonucleotides complementary to the DNA encoding the transmembrane regions as primers for the polymerase chain reaction (PCR) can be successfully employed in the generation of partial DNA sequences encoding proteins having the common transmembrane motif (Libert et al, Science, (1989) 244: 569).

White et al, Trends in Genetics (1989) 5: 179, Arnheim et al, Bioscience (1990) 40: 174 and U.S. Pat. Nos. 4,683,194, 4,683,202 and 4,800,159 all disclose PCR. These are all hereby incorporated by reference.

The inventors have adapted a parallel strategy to the cloning of the entire gene encoding a histamine H2 receptor using cDNA derived from mRNA isolated from a canine gastric cell source as a template. By taking advantage of the marked homology between receptors linked to G-proteins, the inventors have been successful in cloning a novel gene encoding the H2 subtype of histamine receptors and providing a method for cloning the genes encoding all three subtypes of histamine receptors, despite starting without even rudimentary knowledge of the biochemistry of this receptor.

The present invention relates to the inventors' discovery that by using synthetic oligonucleotides complementary to the DNA encoding two transmembrane regions of known G-protein linked receptors as primers for the polymerase chain reaction, the cloning of a histamine receptor gene by using mRNA from an appropriate cell source as a template is achieved. In the present invention a recombinant gene encoding a protein having the pharmacological activity of a histamine receptor was cloned by use of the polymerase chain reaction (PCR) employing as primers synthetic oligo-nucleotides encoding transmembrane regions of G-linked proteins (designated in FIG. 3 by solid lines above which Roman numerals are placed).

The histamine H2 receptor is found in gastric parietal cells, which are responsible for gastric acid secretion. These cells are isolated from the stomach, and mRNA extracted. Using the mRNA as a template and degenerate oligonucleotides corresponding to the 3rd and/or 6th transmembrane region of other G-protein linked receptors (see e.g., III and VI in FIG. 3 or FIG. 4) as primers, PCR is applied to amplify a portion of the histamine H2 receptor. This amplified segment of DNA is then used as a probe to screen a genomic library and the full sequence gene encoding a histamine H2 receptor isolated.

The pharmacological properties of the receptor encoded in this gene are characterized by expression of the gene in L-cells transformed with a CMVneo vector containing the histamine H2 receptor gene insert. The expressed receptor mediates the production of cyclic AMP in L-cells in response to histamine, and this cyclic AMP response could be inhibited with H2-selective receptor antagonists.

Analogously, by employing two synthetic DNA sequences encoding amino acid sequences substantially homologous (preferably at least 90%, most preferably near 100%) to corresponding transmembrane regions of known G-protein linked receptors as primers, and using mRNA isolated from a cell source known to have significant amounts of the desired receptor (e.g., smooth muscle or capillary cells for the H1 receptor, gastric parietal cells for the H2 receptor, and neural cells for the H3 receptor) as a template, a useful method is provided for obtaining a recombinant genomic clone encoding the H1, H2 and H3 histamine receptors.

The present invention thus provides recombinant genomic clones encoding human histamine H1, H2 and H3 receptors produced by the method above in which DNA sequences encoding oligopeptides having homology to transmembrane regions of known G-protein linked receptors are used as primers for the PCR. Messenger RNA is isolated from an appropriate cell source for use as a template for the PCR, to amplify a portion of the gene to which the above primers anneal. The products of the PCR are then used as a probe to screen a genomic library, by which the full sequence gene can be isolated and identified.

Alternatively, once the protein or DNA sequences are known, e.g., per the description given herein, such proteins and DNA sequences can be obtained by using known methods of DNA synthesis, protein synthesis or isolation of such materials from biological sources.

2. Histamine H1, H2 and H3 Receptor Genes and Proteins

In one embodiment, the present invention provides the DNA sequences set forth in FIGS. 1 and 2, and the proteins encoded by these sequences.

In another particularity preferred embodiment, the present invention provides the HUMNH2 and CANH2 transmembrane DNA sequences set forth in FIG. 4 and the proteins encoded by these sequences (SEQ ID NOS:15–16 and 26–27), where each transmembrane sequence may optionally have at each end a further DNA sequence encoding up to 120 amino acids, each amino acid being independently selected from the group of amino acids set forth in Table 1 supra.

The DNA sequences provided by the invention may be cloned into an appropriate known vector using known techniques, which is then used to transform an appropriate microorganism using known techniques. For example, transfection can be carried out by standard procedures, e.g., CaCl$_2$ treatment (Lawnbrook et al, "Molecular Cloning: Laboratory Manual," 2nd ed., Cold Spring Harbor Laboratory, Cold Spring Harbor, N.Y. (1989)). A preferred transfection procedure is calcium phosphate precititation (Okayama et al, *Mol. Cell. Biol.*, (1977) 7: 2745). Any known vectors can be used, including CMVneo or DOL— (Korman et al, *Proc. Nat. Acad. Sci. (USA)* (1987) 84: 2150–2154). Any known microorganisms can be used, including *Eschericia coli*.

3. Uses of the DNA Sequences and Proteins

Currently, there are few, if any, histamine antagonists selective for a particular subclass. The proteins and DNA sequence of the invention encoding each of the histamine receptors can be used as analytical tools for the development of compounds useful for the treatment of allergies, acid-peptic disorders, and neural and cognitive dysfunction. They provide a uniquely effective means for screening for compounds having the best such activity.

The DNA sequence of the histamine receptors provided by the present invention can be used in the development of compounds useful for the treatment of a wide variety of pathologic states in which histamine is involved. For example, the usefulness of H2 blockers in the treatment of acid peptic disorders is well known. However, despite the great selectivity of the H2 blockers presently are clinical, all are known to have some undesirable side effects. Development of even more selective antagonists can stem from a more complete understanding of the molecular structure of the H2 receptor provided by the present invention.

Similarly, superselective H1 antihistamines can be developed that act as cold medications which have fewer side effects than those presently in use. Histamine has a well recognized role in the inflammatory response. More useful antihistamines than those presently known would be developed as anti-inflammatory drugs useful in the treatment of inflammatory conditions, anaphylaxis, as well as for immune modulation. H3 receptors are thought to be auto-regulatory to histamine release. They are present in the brain and peripheral tissues such as the lung, spleen and skin. In peripheral tissues the H3 receptors probably present on the mast cell period histamine release by such mast cells plays a major role in several pathologic processes, most notably asthma. Modulation of this release is the strategy for the treatment of that disease.

All presently known subclasses of histamine receptor are present in the central nervous system. Some of the side effects of known H2 blockers used in the treatment of acid peptic disorders and some side effects of psychotropic used in the treatment of depression and psychosis are attributable to the inscriminent involvement of the various brain histamine receptor subclasses by these drugs. Development of more selective drugs would obviate these effects. Moreover, through a better basic understanding of the physiologic role of the central histamine receptors, histamine agonists and antagonists might be used themselves in the treatment of mental illness.

Histamine is known to affect the cardiovascular system both by its action in the central nervous system and through its effects on the heart and the peripheral smooth muscle. A more basic understanding of the histamine receptor could lead to the development of drugs useful as antihypertensives. Indeed, it is the vast and varied actions of histamine on multiple organ systems (actions which are mediated through its cellular receptor) that has hampered research and development of even more clinically useful histamine agonists and antagonists.

Having generally described this invention, a further understanding can be obtained by reference to specific examples which are provided herein for purposes of illustration only, and are not intended to be limiting.

EXAMPLE

Using the technique of polymerase chain reaction (PCR) with degenerate oligonucleotide primers based on the homology that exists between transmembrane domains of receptors linked to guanine nucleotide binding proteins a canine parietal cell histamine H2 receptor and the human homologue of the canine H2 receptor were isolated. Oligonucleotide primers based on the canine sequence were used to generate a partial length human H2 receptor from human gastric fundus mucosa utilizing the PCR. The partial length human clone was then random primed and used to screen a human genomic library. A full length genomic clone was obtained. Analysis of the homology between the canine and human H2 receptor clones reveals extensive homology between canine and human receptors.

Materials and Methods for Cloning the Human H2 Receptor

Isolation of Messenger RNA.

Human gastric fundus mucosa was obtained from a fresh surgical specimen and placed into liquid nitrogen for storage. The frozen tissue was pulverized and total RNA was extracted by the acid guanidinium thiocyanate-phenol-chloroform method (Chomczynski et al, *Analytical Biochem.* (1987) 162: 156–159). Poly A+RNA was obtained by oligo d(T) cellulose chromatography. The poly A+RNA served as a template for cDNA synthesis using the avian myeloblastosis virus reverse transcriptase (Seikagaku, Rockville, Md.). The cDNA thus obtained functioned as a templated for the polymerase chain reaction with the oligonucleotide primers described below.

Polymerase Chain Reaction.

Three 17mer oligonucleotides that had been used to sequence the canine H2 clone were pooled and used as 5'PCR primers. The three 5'PCR primers had the nucleotide sequences 5'CAGGATGATATCTAACG3' (SEQ ID NO:38), 5'GTGTCGTTGGCTATCACC3' (SEQ ID NO:39), 5'TCCATTCTTAACCTCTT3' (SEQ ID NO:40). The 3'PCR primer had the nucleotide sequence (SEQ ID NO:41)

A reverse complement 17mer which was a degenerate oligonucleotide corresponding to an area in the fifth transmembrane domain of the canine H2 receptor was used as the 3'PCR primer. All oligonucleotides were synthesized using an Applied Biosystems 380B DNA synthesizer. The conditions for the PCR were as follows: denaturation for 1.5 min at 94° C., annealing for 2 min at 45° C., and extension for 4 min at 72° C. The reaction was carried out for 30 cycles and then 20% of the product was added to fresh buffer and submitted to another 30 cycles. The final reaction products were phenol chloroform extracted and then ethanol precipitated. Klenow treatment to blunt-end the DNA was performed and the products of the reaction were electrophoresed on a 1% NuSieve, 1% Seaplaque gel (FMC; Rockland, Me.). Two bands of approximately 575 bp and 400 bp were obtained. The larger band was cut-out of the gel and subcloned directly into the M13 sequencing vector (Crouse et al, "Methods in Enzymology" (1983) 101: 78–79). Dideoxynucleotide sequencing was then performed by the chain termination method of Sanger (*Proc. Nat. Acad. Sci. (USA)* (1977) 74: 5463–5467) using Sequenase Version 2 (USB, Cleveland, Ohio).

Genomic Cloning.

The partial length PCR derived clone was random primed (Vogelstein et al, *Analytical Biochemistry* (1983) 132: 6–13) with $^{32}$P and used as a probe to screen a human genomic library (Clontech, Palo Alto, Calif.). Under high stringency hybridization 0.9M sodium chloride 0.09M sodium citrate (6×SSC), 65° C. and wash conditions (0.1×SSc, 55° C.) a single clone exhibited a positive hybridization signal with the probe. The DNA insert in this clone was restricted mapped and a Pst I fragment that contained the partial length PCR derived clone was inserted into the M13 vector and sequenced. A second Pst I fragment corresponding to the 3' portion of the coding region (bp 916 to the stop codon) and including the untranslated 3' region of the gene was also subcloned into M13.

Northern Blot Analysis

Results:

Of four clones obtained by subcloning the DNA present in the PCR generated gel fragment into M13 one clone had approximately 85% nucleotide homology to the canine histamine H2 receptor. Using this 575 bp PCR generated fragment as a random primed probe we obtained a full length human genomic H2 receptor. The nucleotide sequence (SEQ ID NO:1) of the human receptor is shown in comparison to the canine H2 receptor in FIG. 1. There is 86.8% overal homology in the coding region between the human and canine H2 receptor at a nucleotide level. The amino acid homology between the human and canine clones is shown in FIG. 4. There is 84.7% overall amino acid homology and 90.6% similarity of the amino acids. Homology between canine and human sequences in the extracellular regions, intracytoplasmic portions, and transmembrane domains is shown in Table 2.

Table 2—Percentage nucleotide homology and percentage amino acid identity and similarity of the human H2 receptor coding region in comparison to the canine H2 receptor. Intracytoplasmic, extracellular, and transmembrane regions are divided for separate comparison.

TABLE 2

|  | nucleotide | amino acid % similarity | amino acid % identity |
| --- | --- | --- | --- |
| intracytoplasmic 1 | 82.1 | 92.3 | 92.3 |
| intracytoplasmic 2 | 88.3 | 95.0 | 90.0 |
| intracytoplasmic 3 | 90.0 | 96.7 | 83.3 |
| intracytoplasmic 4 | 85.9 | 78.9 | 75.5 |
| extracellular 1 | 78.8 | 81.8 | 68.2 |
| extracellular 2 | 90.9 | 100 | 90.9 |
| extracellular 3 | 77.8 | 76.2 | 76.2 |
| extracellular 4 | 96.3 | 100 | 88.9 |
| transmembrane 1 | 80.3 | 86.4 | 72.7 |
| transmembrane 2 | 90.3 | 95.8 | 87.5 |
| transmembrane 3 | 86.4 | 95.5 | 90.9 |
| transmembrane 4 | 92.0 | 100 | 96.0 |
| transmembrane 5 | 91.7 | 100 | 95.8 |
| transmembrane 6 | 86.1 | 95.8 | 95.8 |
| transmembrane 7 | 85.9 | 78.9 | 75.5 |

Several amino acids in the amino and carboxy terminus of the third intracytoplasmic loop which are thought to be important to binding to the stimulatory G-protein (Gs) are identical in the human and canine clones are highlighted in FIG. 4.

Discussion

Several features of interest are present in a comparison of the human and canine H2 receptor sequences. An out-of-frame ATG codon 50 base pairs upstream of the presumed initiation codon of the major open reading frame of the anine H2 receptor sequence is not present in the human clone. A similar short open reading frame can be noted in the beta adrenergic receptor. The absence of the short open reading frame in the human clone might be interpreted to mean a lack of significance for this occurrance in the H2 receptor.

The fifth transmembrane of the human and canine H2 receptor are 94.7% homologous at an amino acid level (SEQ ID NOS:26–27) and 93% at a nucleotide level. However, if one looks at the nucleotide sequence of the nine amino acids surrounding and including the aspartic acid and threonine portion of this domain (V, D, G, L, V, T, F, Y, L) there is 100% homology at a nucleotide and amino acid level. Mutational analysis of the beta adrenergic receptor has suggested that the fifth transmembrane serine residues are important in forming hydrogen bonds to the hydroxyl groups of the catechol ring of adrenergic agonists. By analogy the aspartic acid and threonine in the fifth transmembrane domain of our H2 receptor have the potential to interact with the imidizole ring of histamine. The absolute nucleotide sequence homology in this stretch supports the possibility of such an interaction.

Mutational analysis of the beta adrenergic receptor has also suggested that critical area of interaction with the stimulatory G-protein ($G_s$) reside in the amino acids A, K, R at the amino terminus and E, H, K, A of the third intracytoplasmic loop (13). The H2 receptor present on the canine parietal cell which is known to act predominantly through Gs fully maintains this sequence. There is little information about the second messenger signaling pathway of the human parietal cell H2 receptor. The human H2 clone has complete conservation of these amino acids in the third intracytoplasmic loop. However, in view of the second messenger signaling pathways described for the H2 receptor which has been pharmacologically characterized on the HL60 cell and the rabbit parietal cell one must be careful before concluding that the human clone can work only through $G_s$ and cAMP.

Isolation of Canine Histamine H2 Receptor:

Cells from freshly obtained canine fundic mucosa were dispersed by sequential exposure to crude collagenase (0.25 µg/ml) and EDTA (1 mM) and a fraction enriched in parietal cells (approximately 70%) was isolated by counterflow elutriation according to the method of Soll (*J. Clin. Invest.* (1978) 61: 370). RNA was extracted by the acid guanidinium thiocyanate-phenol-chloroform method (Sanger et al, *Proc. Natl. Acad. Sci. (USA)* (1977) 74: 5463), and poly $A^+$ RNA was obtained by oligo(T) cellulose chromatography.

The poly $A^+$ RNA served as a template for cDNA synthesis using the avian myeloblastosis virus reverse transcriptase and the cDNA thus obtained functioned as a template for the polymerase chain reaction using as primers oligonucleotides corresponding to the third and sixth transmembrane domains of G-protein linked receptors as described by Libert et al (*Science* (1989) 244: 569). The conditions for the polymerase chain reaction were as follows: denaturation for 1.5 min. at 93° C., annealing for 2 min. at 4° C., and extension for 4 min. at 72° C. The reaction was carried out for thirty cycles, then 20% of the product was added to fresh buffer and submitted to another 30 cycles. The final reaction products were ethanol precipitated and electrophoresed on a 2% NuSieve, 1% Seaplaque gel (FMC, Rockland, Me.).

The band of approximately 500 base pairs in length was phenol-extracted from the electrophoresis gel, blunt ended using the Klenow fragment of DNA polymerase and subcloned into M13. The nucleotide sequence was determined, and computer analysis of the deduced amino acid sequence revealed extensive homology to other known G-protein linked receptors. Kyte-Doolittle analysis confirmed the presence of the two hydropathic putative transmembrane domains between the third and sixth transmembrane sequences upon which the primers were based (Kyte et al, *J. Mol. Biol.* (1982) 157: 105).

This partial length polymerase chain reaction derived clone was random primed (Vogelstein et al, *Analytical Biochemistry* (1983) 132: 6) with $^{32}P$ and used as a probe to screen a canine genomic library (Clontech, Palo Alto, Calif.). Under high stringency hybridization and wash conditions (65° C., 15 mM sodium chloride, 1.5 mM sodium citrate, 55° C.) a single clone exhibited a positive hybridization signal with the probe. The nucleotide sequence (SEQ ID NO:5) and deduced corresponding amino acid sequence (SEQ ID NO:6) of the presumed coding region of this gene is depicted in FIG. 2. The GenBank data base accession number is M 32701.

Comparison of the deduced amino acid sequence to that of other G-protein linked receptors revealed extensive homology with other members of this family (FIG. 3). Like the genes encoding many of the other members of this family, the gene appeared to be devoid of introns as well (Kobilka et al, *J. Biol. Chem.* (1987) 262: 15796).

Several features of the amino acid sequence deduced from our cloned gene were notable and provided clues as to the natural ligand for the receptor that it encoded. The aspartic acid residue in the third transmembrane domain has been shown by mutational analysis to be important for ligand binding to the beta adrenergic receptor. It is hypothesized that the carboxyl group of the aspartic acid moiety acts as a counter anion to the cationic amino group of beta adrenergic agonists (Strader et al, *J. Biol. Chem.* (1988) 263: 10267). Indeed, receptors for a number of cationic biogenic agonists such as dopamine and acetylcholine are also characterized by the presence of this aspartic acid residue while receptors for other ligands are not.

The second structural feature of note was the absence of the two serine residues present in the fifth transmembrane region of receptors for catecholamines and dopamine as highlighted in FIG. 4. This information suggests that our clone encodes a novel class of receptor. However, the conservative substitution of a threonine and aspartic acid for the two serine residues was of particular interest in view of the data suggesting that the serines are sites of hydrogen bonding to the hydroxyl groups present in the catechol ring of adrenergic agonists (Strader et al, *FASEB* (1989) 3: 1825).

A third structural feature of interest (FIG. 4) was the relatively truncated third cytoplasmic loop (between the fifth and sixth transmembrane regions) which is characteristic of other receptors such as the beta adrenergic, thyroid stimulating hormone and luteinizing hormone-human chorionic gonadotropin receptors that are linked to stimulatory G-proteins associated with induction of adenylate cyclase. (Lefkowitz et al, *J. Biol. Chem.* (1988) 262: 4993; Parmentier et al, *Science* (1989) 246: 1620; Loosfelt et al, *Science* (1989) 245: 525; Ross, *Nature* (1990) 344: 707). In this region of the third cytoplasmic loop, the greatest area of homology between the receptor encoded by our clone and beta adrenergic receptors appeared to be at both carboxyl and amino terminal ends which have been shown previously to be critical to the linkage of G-proteins (Strader et al, *FASEB* (1989) 3: 1825).

This structural information suggests the possibility that the clone encodes a receptor for a positively charged biogenic amine linked to adenylate cyclase activation. The most likely receptor on gastric parietal cells fitting this description is the H2 subtype of histamine receptor. To test this hypothesis, several constructs that contained the presumed coding region of the receptor gene were inserted into the eukaryotic expression vector CMVneo and expressed in mouse L-cells. After transfection of the expression vector by calcium phosphate precipitation (Okayama et al, *Mol. Cell. Biol.* (1987) 7: 2745), the permanently transfected L-cells were selected by adding 600 ug/L of the neomycin analogue G418 to the culture medium.

Response to Exogenously Administered Histamine:

Response to exogenously administered histamine of L-cells transfected with a CMVneo vector containing the canine histamine H2 receptor gene insert is shown in FIG. 5. Cells were incubated in Earle's balanced salt solution with varying concentrations of histamine for 60 min. at 37° C. after 60 min pre-incubation either in medium with or without addition of cimetidine ($10^{-4}M$). Ice cold 30% trichloroacetic acid was added to stop the reaction and precipitate the cellular protein. After centrifugation for 10 min. at 1,000 g, the supernatant was ether extracted, lyophilized, and re-suspended in 50 mM Tris, 2 mM EDTA, pH 7.5. The content of cyclic AMP was measured by competitive protein binding assay using an Amersham kit (Arlington Heights, Ill.).

The transfected cells demonstrated dose-dependent increases in cellular cyclic AMP content in response to histamine stimulation (FIG. 5) reaching a maximum of 217±10% over basal (mean±se, n=3) after the $10^{-5}$M histamine dose. The dose-response curve could be shifted to the right by the H2 receptor selective antagonist cimetidine. Serotonin, epinephrine, dopamine and carbamoylcholine in doses as high as $10^{-4}$M had no effect on cAMP content. Non-transfected L-cells, L-cells transfected with a CMVneo vector missing the receptor gene construct insert, and L-cells transfected with a CMVneo vector containing as an insert a gene encoding the alpha catalytic subunit of the cyclic AMP dependent protein kinase all failed to demonstrate any response to histamine.

Figure 6:
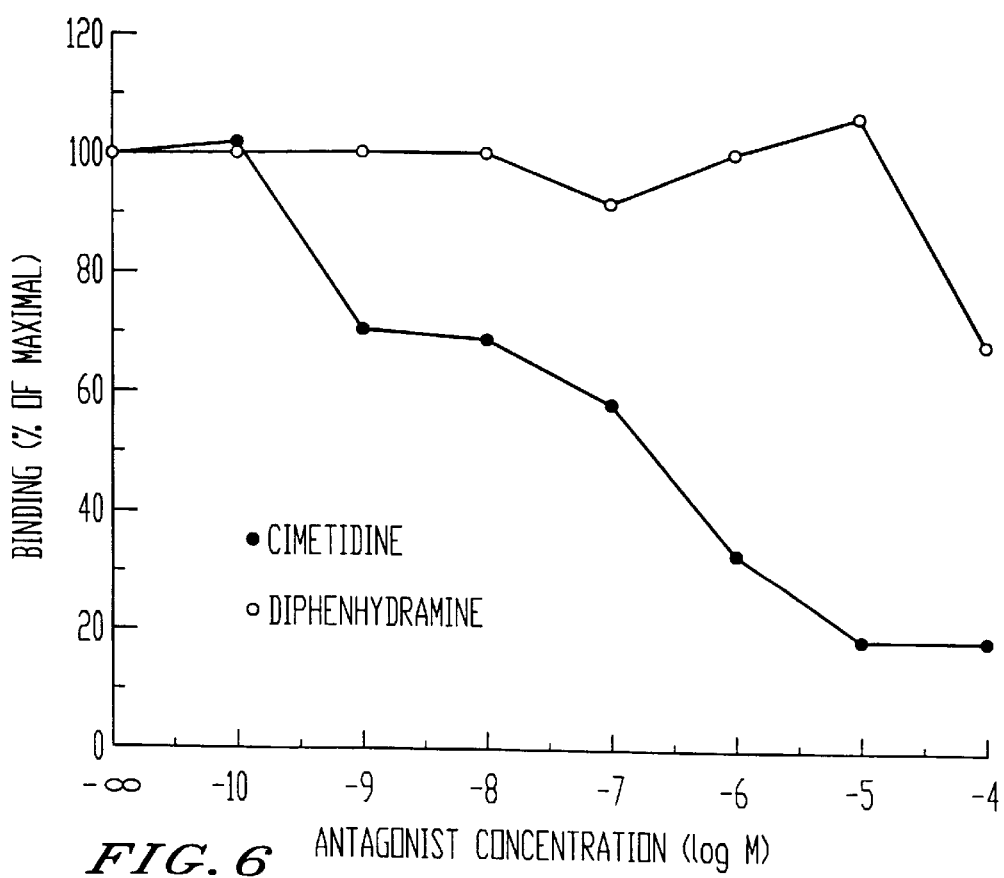
FIG. 6 shows a graph displaying the inhibition of [methyl-$^3$H]-tiotidine binding to transformed L-cells by diphenhydramine and cimetidine.

Competitive Binding with Known Histamine Receptor Antagonists:

Inhibition of [methyl-$^3$H]-tiotidine binding to transformed L-cells by diphenhydramine and cimetidine is shown in FIG. 6. Transformed L-cells were plated and grown to confluence in 2.4×1.7 cm multi-well plates. The culture media was removed and cells were washed twice with Earle's balanced salt solution containing 0.1% bovine serum albumin. An aliquot (36 nCi) of [methyl-$^3$H]-tiotidine (87 Ci/mmol; Dupont, Boston Mass.) was added to the culture in the presence of either cimetidine or diphenhydramine and after one hour of incubation, the medium was removed by aspiration. The cells were washed twice with 0.2M phosphate buffered NaCl pH 7.4, lysed with 1% Triton X-100, and the radioactivity was quantified. Maximum binding was determined by incubation of [methyl-$^3$H]-tiotidine with transformed L-cells in the absence of antagonists and non-specific binding, which was subtracted from total binding to obtain specific binding, was determined as the amount of label remaining bound in the presence of $10^{-4}$M histamine. The data, presented as percent of maximal specific binding, are from a single experiment and are virtually identical to data obtained in two other experiments. The H2 receptor selective antagonist cimetidine dose-dependently inhibited label binding whereas diphenhydramine, an H1 selective antagonist, inhibited binding only at the very highest dose.

As shown in FIG. 6, cimetidine displaced binding of the ligand in a dose-dependent fashion with an ED50 of $5.5 \pm 0.6 \times 10^{-7}$M (mean±se n=4). In contrast, diphenhydramine, a relatively selective H1 receptor antagonist, demonstrated no ability to inhibit [methyl-$^3$H]-tiotidine except with the highest dose. These data indicate that this clone encodes a novel protein with the pharmacological properties of the H2 subtype of histamine receptor.

An interesting feature of our cloned gene is the presence of an out-of-frame ATG codon 52 base pairs upstream of the presumed initiation codon of the major open reading frame. A similar short open reading frame upstream of the major open reading frame has been described previously for the beta adrenergic receptor although its significance is yet unknown (Dixon et al, *Nature* (1986) 321: 75; Allen et al, *Molecular Pharmacology* (1989) 36: 248). The translation initiation sequence of the major open reading frame is more consistent with the consensus eukaryotic translation initiation sequence (Kozak, *Nucleic Acids Research* (1983) 12: 857). The transcription initiation site of the receptor gene has not been determined; however, we examined three different receptor gene constructs in L-cells, one containing the entire gene sequence as described in FIG. 2 and the other two lacking the short upstream open reading frame. Expression of all these constructs resulted in L-cells that exhibited histamine binding and cyclic AMP generation in response to histamine. Thus the upstream segment is apparently not essential for histamine receptor gene expression.

Obviously, numerous modifications and variations of the present invention are possible in light of the above teachings. It is therefore to be understood that within the scope of the appended claims, the invention may be practiced otherwise than as specifically described herein.

---

What is claimed as new and desired to be secured by Letters Patent of the United States is:

1. A DNA sequence encoding a protein having H2 receptor activity and the amino acid sequence:
MAPNGTASSFCLDSTACKITITVVLAV-LILITVAGNVVVCLAVGLNRRLRNLTNCFIVSLAI TDLLLGLLVLPFSAIYQLSCKWSF-GKVFCNIYTSLDVMLCTASILNLFMIS-LDRYCAVMDPL RYPVLVTPVRVAISLVLIWVISITLS-FLSIHLGWNSRNETSKGNHTTSKCKVQVNEVYGLVD GLVTFYLPLLIMCITYYRIFKVARD-QAKRINHISSWKAATIREHKATVTLAAVMGAFIICWF PYFTAFVYRGLRGDDAINEVLEAIVL-WLGYANSALNPILYAALNRDFRTGYQQLFCCRLANR NSHKTSLRSNASQLSRTQSREPRQQEEK-PLKLQVWSGTEVTAPQGATDR (SEQ ID NO:2).

2. A DNA sequence encoding a protein having H2 receptor activity and the amino acid sequence:
MISNGTASSFCLDSPPCRITVSVVLTV-LILITIAGNVVCLAVGLNRRLRSLTNCFIVSFSI TDLLLGLLVLPFSAFYQLSCRWSF-GKVFCNIYTSLDVMLCTASILNLFMIS-LDRYCAVTDPL RYPVLITPVRVAVSLVLIWVISITLS-FLSIHLGWNSRNETSSFNHTIPKCKVQVNLVYGLVD GLVTFYLPLLVMCITYYRIFKI-ARDQAKRIHHMGSWKAATIGEHKATVT-LAAVMGAFIICWF PYFTVFVYRGLKGDDAINEAF-EAVVLWLGYANSALNPILYATLNRDFRTAYQQLFRCRPASH NAQETSLRSNSSQLARNQSREPMRQEEK-PLKLQVWSGTEVTAPRGATDR (SEQ ID NO:4).

3. The DNA sequence according to claim 1, wherein the peptide encoded is the human histamine H2 receptor.

4. The DNA sequence according to claim 2, wherein the peptide encoded is the canine histamine H2 receptor.

5. A transfer vector comprising the DNA sequence encoding a protein having histamine H2 receptor according to claim 2.

6. A transfer vector comprising the DNA sequence encoding a protein having histamine H2 receptor according to claim 1.

7. A microorganism transformed with the transfer vector of claim 5.

8. A microorganism transformed with the transfer vector of claim 6.

* * * * *

UNITED STATES PATENT AND TRADEMARK OFFICE
CERTIFICATE OF CORRECTION

PATENT NO. : 5,885,824

DATED : March 23, 1999

INVENTOR(S): Tadataka YAMADA, et al.

It is certified that an error appears in the above-identified patent and that said Letters Patent is hereby corrected as shown below:

Column 2, line 34, "sequences (SEQ ID NO:6). FIG 2"
 should read --sequences. FIG 2--;

line 35, "sequence of" should read --sequence (SEQ ID NO:6) of --.

Column 7, line 66, "overal" should read --overall--.

Column 15, lines 5 and 6, "Pro Gln Gly Ala Thr Asp Arg
 355"
 should read --Pro Gln Gly Ala Thr Asp Arg
 355 360--.

Column 19, lines 41 and 42, "CCT CGA GGA GCC ACA GAC AGG TAA"
 should read --CCT CGA GGA GCC ACA GAC AGG TAA
 1077--.

line 49, "359 amino" should read --360 amino--.

Signed and Sealed this

Tenth Day of April, 2001

NICHOLAS P. GODICI

Attest:

Attesting Officer    Acting Director of the United States Patent and Trademark Office